United States Patent [19]

Samal

[11] Patent Number: 5,580,754
[45] Date of Patent: Dec. 3, 1996

[54] NUCLEIC ACID ENCODING THE PROGENITOR B CELL STIMULATING FACTOR

[75] Inventor: Babru B. Samal, Moorpark, Calif.

[73] Assignee: Amgen Inc., Thousand Oaks, Calif.

[21] Appl. No.: 294,770

[22] Filed: Aug. 23, 1994

Related U.S. Application Data

[63] Continuation of Ser. No. 980,524, Nov. 20, 1992, abandoned.

[51] Int. Cl.⁶ .................................................. C12N 15/12
[52] U.S. Cl. .................. 435/69.5; 435/240.2; 435/252.3; 435/254.11; 435/320.1; 536/23.5
[58] Field of Search ................... 435/69.5, 240.1, 435/252.3, 254.11, 320.1, 240.2; 536/23.1, 23.5

[56] References Cited

U.S. PATENT DOCUMENTS

| | | | |
|---|---|---|---|
| 4,179,937 | 12/1979 | Davis et al. | 435/181 |
| 4,710,473 | 12/1987 | Morris et al. | 435/320 |
| 4,965,195 | 10/1990 | Namen et al. | 435/69.52 |
| 4,999,291 | 3/1991 | Souza et al. | 435/69.1 |
| 5,066,581 | 11/1991 | Suciu-Focal et al. | 435/7.24 |

FOREIGN PATENT DOCUMENTS

| | | |
|---|---|---|
| WO89/06541 | 7/1989 | WIPO. |
| WO91/05795 | 5/1991 | WIPO. |

OTHER PUBLICATIONS

Arai et al. Ann Rev. Biochem. 59, 783 (1990).
Billips et al. Blood 79, 1185 (1992).
Brach et al. Acta. Haematol. 86, 128 (1991).
Chirgwin et al. Biochemistry 18, 5294 (1979).
Hodgson et al. Nature 281, 381 (1979).
Hunkapillar et al. Methods in Enzymol 91, 227 (1983).
Johnson et al. Dev. Biol. Stand. 69, 3 (1988).
Lehrach et al. Biochem. 16, 4743 (1977).
Liu et al. Biochem. 18, 690 (1979).
Maniatis et al. Molecular Cloning, A Laboratory Manual (1982), 197–198, Cold Spring Harbor Laboratory, Cold Spring Harbor.
Martin et al. Cell. 63, 203 (1990).
May et al. PNAS 83, 8957 (1986).
McNiece et al. J. Immunol. 146, 3785 (1991).
Metcalf et al. Proc. Natl. Acad. Sci. 88, 111310 (1991).
Migliaccio et al. J. Cell Physiol. 148, 503 (1991).
Miller et al. Biotechnique 7, 980 (1989).
Miller et al. Mol. Cell. Biol. 6, 2895 (1986).
Nishida et al. Biochem. Biophys. Res. Commun. 143, 345 (1987).
Noonan et al. Nucleic Acid Res. 16, 10366 (1988).
Okayama et al. Methods Enzymol. 154, 3 (1987).
Olofsson et al. Acta Oncol. 30, 889 (1991).
Ponting et al. Growth Factors 4, 165 (1991).
Nairn, Remington Pharmaceutical Sciences (1990), 1519–1544, Mack Publishing Company, Easton, Pennsylvania.
Samal et al. Leuk. Res. 14, 575–580 (1990).
Sanger et al. PNAS 74, 5463 (1977).
Shaw et al. Cell 46, 659 (1986).
Taniguchi et al. Nature 302, 305 (1983).
Von Heijne et al. Nucleic Acid Res. 14, 4683 (1986).
Wong et al. Science 228, 810 (1985).
Yang et al. Cell. 47, 370 (1986).

Primary Examiner—Stephen G. Walsh
Assistant Examiner—Sally P. Teng
Attorney, Agent, or Firm—Robert B. Winter

[57] ABSTRACT

A progenitor B cell stimulating factor which promotes the formation of pre-B cells is described. DNA sequences encoding same and methods of production and purification of the factor are also disclosed. The factor is used in the treatment of hematopoietic disorders and in bone marrow transplantation.

12 Claims, 16 Drawing Sheets

```
ACT GTG GCC  TGC  AGC  ATC  TCT  GCA  CCC  GCC  CGC  TGC  CCC AGC CCC  GM
CTT GCA CTT  GTC  ACA  AAC  AGT  GCA  CCT  ACT  TCA  AGT  TCT ACA AAG  IL2
AAC GAG GCT  TAT  GTG  CAC  GAT  GCA  CCT  GTA  CGA  TCA  CTG AAC TGC  IL1B
GTG TTG CCT  GCT  GCC  TCC  CCT  GCC  CCA  GTA  CCC  CCA  GGA GAA GAT  IL6
CTG GTC CGC  CCC  GGA  CTC  CAA  GCT  CCC  ATG  ACC  CAG  ACA ACG CCC  IL3

AT GTC  GAC  CAC  GCT  GCC  CCA  ACC  CGA  CCC  A
                        AT   CA     A    C  GTA  TCC  T A
                              G          T
```

FIG. 1

```
CGC GCG GCC CCT GTC CTC CGG CCC GAG ATG AAT CCT GCG GCA GAA
                                    Met Asn Pro Ala Ala Glu
        1 0              30                      90
                                 7 0

GCC GAG TTC AAC ATC CTC CTG GCC ACC GAC TCC TAC AAG GTT ACT
Ala Glu Phe Asn Ile Leu Leu Ala Thr Asp Ser Tyr Lys Val Thr
  50               1 10                        1 3 0

CAC TAT AAA CAA TAT CCA CCC AAC ACA AGC AAA GTT TAT TCC TAC
His Tyr Lys Gln Tyr Pro Pro Asn Thr Ser Lys Val Tyr Ser Tyr
               150                       1 70

TTT GAA TGC CGT GAA AAG ACA AAG GAA AAC TCC AAA TTA AGG AAG
Phe Glu Cys Arg Glu Lys Thr Lys Glu Asn Ser Lys Leu Arg Lys
        19 0                     210

GTG AAA TAT GAG GAA ACA GTA TTT TAT GGG TTG CAG TAC ATT CTT
Val Lys Tyr Glu Glu Thr Val Phe Tyr Gly Leu Gln Tyr Ile Leu
               2 30                  25 0

AAT AAG TAC TTA AAA GGT AAA GTA GTA ACC AAA GAG AAA ATC CAG
Asn Lys Tyr Leu Lys Gly Lys Val Val Thr Lys Glu Lys Ile Gln
                                                       270
```

FIG. 2A

```
GAA GCC AAA GAT GTC TAC AAA GAA CAT TTC CAA GAT GAT GTC TTT
Glu Ala Lys Asp Val Tyr Lys Glu His Phe Gln Asp Asp Val Phe
                    290                            310

AAT GAA AAG GGA TGG AAC TAC ATT CTT GAG AAG TAT GAT GGG CAT
Asn Glu Lys Gly Trp Asn Tyr Ile Leu Glu Lys Tyr Asp Gly His
                330                            350
           370                            390

CTT CCA ATA GAA ATA AAA GCT GTT CCT GAG GGC TTT GTC ATT CCC
Leu Pro Ile Glu Ile Lys Ala Val Pro Glu Gly Phe Val Ile Pro
     410                            430                    450

AGA GGA AAT GTT CTC TTC ACG GTG GAA AAC ACA GAT CCA GAG TGT
Arg Gly Asn Val Leu Phe Thr Val Glu Asn Thr Asp Pro Glu Cys
                    470                            490

TAC TGG CTT ACA AAT TGG ATT GAG ACT ATT CTT GTT CAG TCC TGG
Tyr Trp Leu Thr Asn Trp Ile Glu Thr Ile Leu Val Gln Ser Trp
                510                            530

TAT CCA ATC ACA GTG GCC ACA AAT TCT AGA GAG CAG AAG AAA ATA
```

```
                                                         550
Tyr Pro Ile Thr Val Ala Thr Asn Ser Arg Glu Gln Lys Lys Ile
TTG GCC AAA TAT TTG TTA GAA ACT TCT GGT AAC TTA GAT GGT CTG
Leu Ala Lys Tyr Leu Leu Glu Thr Ser Gly Asn Leu Asp Gly Leu
        590                  610                  630
GAA TAC AAG TTA CAT GAT TTT GGC TAC AGA GGA GTC TCT TCC CAA
Glu Tyr Lys Leu His Asp Phe Gly Tyr Arg Gly Val Ser Ser Gln
                                          650                  670
GAG ACT GCT GGC ATA GGA GCA TCT GCT CAC TTG GTT AAC TTC AaA
Glu Thr Ala Gly Ile Gly Ala Ser Ala His Leu Val Asn Phe Lys
                    690                                       710
GGA ACA GAT ACA GTA GCA GGA CTt GCT CTA ATT AAA TAT TAT TAT
Gly Thr Asp Thr Val Ala Gly Leu Ala Leu Ile Lys Lys Tyr Tyr
        730                                       750
GGA ACG AAA GAT CCT GTT CCA GGC TAT TCT GTT CCA GCA GCA GAA
Gly Thr Lys Asp Pro Val Pro Gly Tyr Ser Val Pro Ala Ala Glu
                            770                  790                  810
CAC AGT ACC ATA ACA GCT TGG GGG AAA GAC CAT GAA AAA GAT GCT
His Ser Thr Ile Thr Ala Trp Gly Lys Asp His Glu Lys Asp Ala
```

FIG. 2D

```
TTT GAA CAT ATT GTA ACA CAG TTT TCA TCA GTG CCT GTA TCT GTG
Phe Glu His Ile Val Thr Gln Phe Ser Ser Val Pro Val Ser Val
              870                       890              850

GTC AGC GAT AGC TAT GAC ATT TAT AAT GCG TGT GAG AAA ATA TGG
Val Ser Asp Ser Tyr Asp Ile Tyr Asn Ala Cys Glu Lys Ile Trp
                              930

GGT GAA GAT CTA AGA CAT TTA ATA GTA TCG AGA AGT ACA CAG GCA
Gly Glu Asp Leu Arg His Leu Ile Val Ser Arg Ser Thr Gln Ala
   910                                970                 990

CCA CTA ATA ATC AGA CCT GAT TCT GGA AAC CCT CTT GAC ACT GTG
Pro Leu Ile Ile Arg Pro Asp Ser Gly Asn Pro Leu Asp Thr Val
                              1010                      1030

TTA AAG GTT TTG GAG ATT TTA GGT AAG AAG TTT CCT GTT ACT GAG
Leu Lys Val Leu Glu Ile Leu Gly Lys Lys Phe Pro Val Thr Glu
              1050                     1070

AAC TCA AAG GGT TAC AAG TTG CTG CCA CCT TAT CTT AGA GTT ATT
```

FIG. 2E

```
Asn Ser Lys Gly Tyr Lys Leu Leu Pro Pro Tyr Leu Arg Val Ile
                                            1 110
1 090
CAA GGG GAT GGA GTA GAT ATT AAT ACC TTA CAA GAG ATT GTA GAA
Gln Gly Asp Gly Val Asp Ile Asn Thr Leu Gln Glu Ile Val Glu
1 130                     1 150                     1 170
GGC ATG AAA CAA AAA ATG TGG AGT ATT GAA AAT ATT GCC TTC GGt
Gly Met Lys Gln Lys Met Trp Ser Ile Glu Asn Ile Ala Phe Gly
              1 190                     1 210
TCT GGT GGA GGT TTG CTA CAG AAG TTG ACA AGA GAT CTC TTG AAT
Ser Gly Gly Gly Leu Leu Gln Lys Leu Thr Arg Asp Leu Leu Asn
        1 230                     1 250
TGT TCC TTC AAG TGT AGC TAT GTT GTA ACT AAT GGC CTT GGG ATT
Cys Ser Phe Lys Cys Ser Tyr Val Val Thr Asn Gly Leu Gly Ile
1 270                     1 290
AAC GTC TTC AAG GAC CCA GTT GCT GAT CCC AAC AAA AGG TCC AAA
Asn Val Phe Lys Asp Pro Val Ala Asp Pro Asn Lys Arg Ser Lys
```

FIG. 2F

```
1310                                                                        1350
AAG GGC CGA TTA TCT TTA CAT AGG ACG CCA GCA GGG AAT TTT GTT
Lys Gly Arg Leu Ser Leu His Arg Thr Pro Ala Gly Asn Phe Val 1370                              1390
ACA CTG GAG GAA GGA AAA GGA GAC CTT GAG GAA TAT GGT CAG GAT
Thr Leu Glu Glu Gly Lys Gly Asp Leu Glu Glu Tyr Gly Gln Asp 1410                              1430
CTT CTC CAT ACT GTC TTC AAG AAT GGC AAG GTG ACA AAA AGC TAT
Leu Leu His Thr Val Phe Lys Asn Gly Lys Val Thr Lys Ser Tyr 1450                              1470
TCA TTT GAT GAA ATA AGA AAA AAT GCA CAG CTG AAT ATT GAA CTG
Ser Phe Asp Glu Ile Arg Lys Asn Ala Gln Leu Asn Ile Glu Leu 1490                    1510                                1530
GAA GCA GCA CAT CAT TAG GCT TTA TGA CTG GGT GTG TGT GTG
Glu Ala Ala His His End 1550                  1570
```

```
TAT GTA ATA CAT AAT GTT TAT TGT ACA GAT GTG TGG GGT TTG TGT
TTT ATG ATA CAT TAC TTT CAA ATT TTT CCA TGG TTT ATG GAC ATA
CTG CCC TTT CAT TTT TCT CCA TTT TGT GTG TTT AGG TCT AAG CAA
ATT AGG AAA TGC TAA ATT TAA CCA AAA AGA TGA CTA ATC AAG TAA
GCT TTT TAG GGC CCT TAG CCT TTG GGT AGT CAT TCA TGG TAT
TGA TCT TTT CAC AAA TAA CAG GAA ACT TTT ATA TAT AAC
                                1550                      1570
TGA TCA CAT AAA ACA GAT TTG CAT AAA ATT ACC ATG ATT GCT
TTA TGT TTA TAT ACT TTT CAG TGT CAA ACA AGA TTG TGT
AAG ATA TAT TTG AAG TGA TTT AAC AGT CTT TCC AAC TTT
TCA TGA TTT TGA GCA TTG ACT TTC AAG AAA ATA CTT GAA AAT
AAA TTA CAT AAA TGC TTT TGT TCC AAT CAG CCC TGG CAT GGC
CTT GTA ATT GTT CTT GTT GTA ACC CAA TAA CTG TTG TAT TAT
GGG ACA TAC CCT ATC ACT ATA AAT CAG CAA AGA ATC CCC GTA GAA
TAT GTA TTA ATC ATT CTA TTA CAT AGG TTA AGG CCT ATG TTC CTG CTG GTA
GAA TGT CTA GGC GCC GTA TAA CAG AAA TAT AGG TCT GAA ATG CAC CTC GTA
TTT ATG CAG TGA GCC TTT TGT AAA TCT AAT TTT AAT CCT CTT CAA TTT
TAT AGG TCA GAG TAA TTT TAG AGA TCT GAA TAT TGT CTG CTT
TTA AGA CTA CAG TCA TGT AGG GGA AGA ATT AAT GTA CAA AAG CTA
AAT ATA TAC ATA AAT GTA AAT TAC TTA CAA TGG TAG
```

FIG. 2G

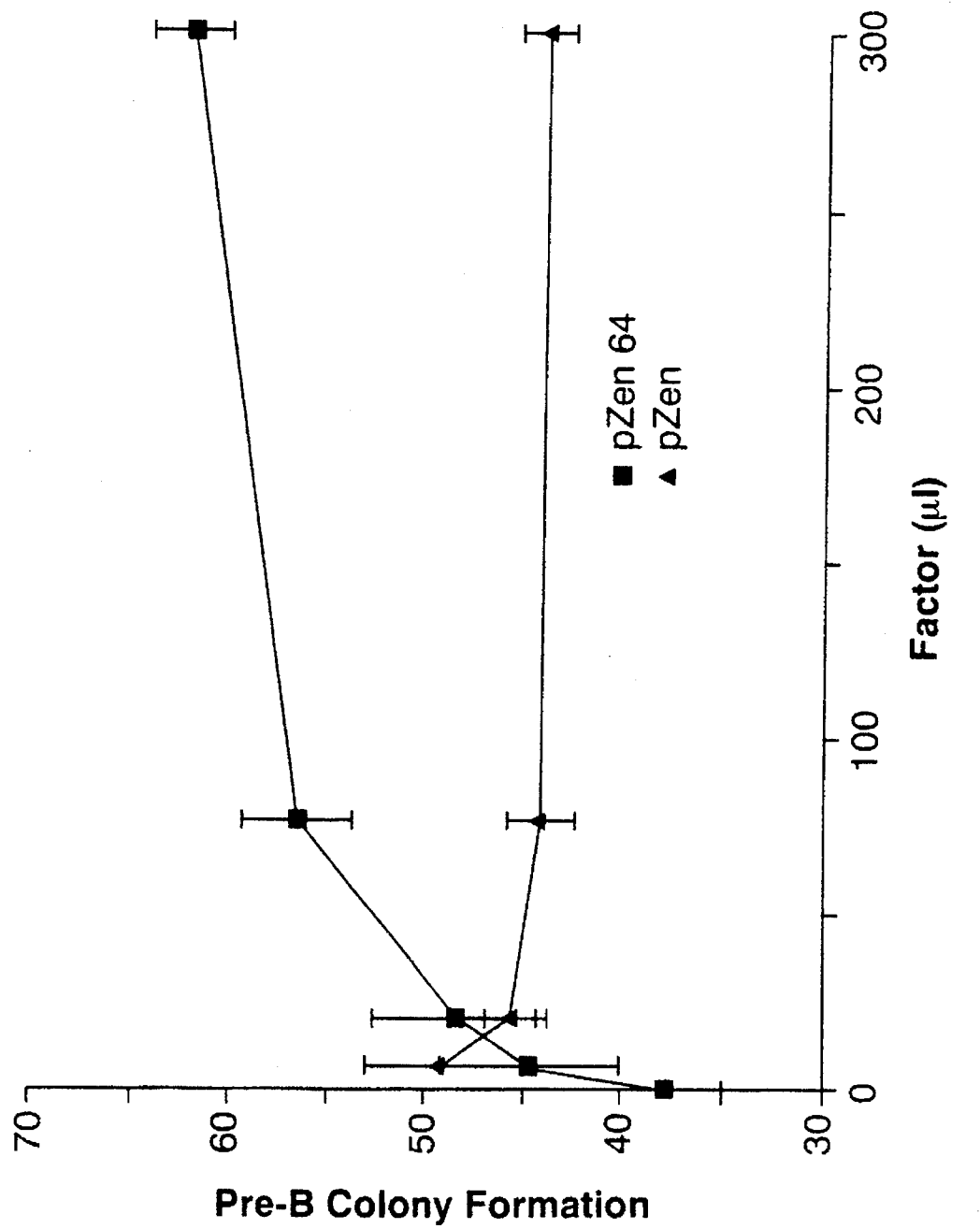

NUCLEIC ACID ENCODING THE PROGENITOR B CELL STIMULATING FACTOR

This application is a continuation of application Ser. No. 07/980,524 filed Nov. 20, 1992, now abandoned, which is hereby incorporated by reference.

The present invention relates to a novel factor, progenitor B cell stimulating factor, having the activity of promoting the proliferation and differentiation of hematopoietic progenitor cells. The invention also relates to DNA sequences encoding such factors, to polypeptide fragments and analogs thereof, and methods and compositions for the treatment of hematopoietic disorders using the factor.

BACKGROUND OF THE INVENTION

Hematopoietic growth factors are the major regulatory molecules supporting constitutive and inducible hematopoiesis (Brach et al. *Acta. Haematol.* 86,128 (1991)). The hematopoietic growth factors (colony stimulating factors and interleukins), growth-factor synergizing factors, and growth factor-releasing factors control the proliferation, differentiation, and functional activation of hematopoietic stem cells and lineage-committed progenitor cells. Each colony stimulating factor has distinct lineages of bone marrow cells upon which they act, although there is some overlap in lineage activity and synergy between colony stimulating factors. In several instances, the involvement of growth factors in the maturation of specific hematopoietic cell types is well known, as in the action of erythropoietin to produce erythrocytes and granulocyte colony stimulating factor to produce neutrophils. However, there are a number of stages in hematopoietic cell development where the identification of stimulatory factors is incomplete or lacking altogether. This is particularly true for those events leading to the proliferation and development of early hematopoietic progenitor cells.

Hematopoietic progenitor cells develop gradually from pluripotent to unipotent, committed progenitor cells during which process they lose their self-renewal capacity (Olofsson *Aca. Oncol.* 30, 889 (1991)). This development is dependent on interactions of specific hematopoietic growth factors, which by binding to surface receptors on the stem cells stimulate them to proceed to the next step of differentiation. Interleukin-3 (IL-3) is primarily a proliferative stimulus for the undifferentiated progenitor cells (Ponting et al. *Growth Factors*, 4, 165 (1991)). Granulocyte Macrophage-Colony Stimulating Factor (GM-CSF) also plays a major role in multipotent stem cell survival, proliferation and differentiation into stem cells with restricted maturation programs. The programmed unipotent stem cells need stimulation by erythropoietin, granulocyte-colony stimulating factor (G-CSF), macrophage colony stimulating factor (M-CSF) and IL-5 to proliferate and mature into their end stage products, erythrocytes, neutrophils, monocytes and eosinophils respectively. Other cytokines such as IL-1β, IL-4 and IL-6 fulfill important functions as cofactors in these processes (Arai et al. *Ann. Rev. Biochem.* 59, 783 (1990)).

Stem cell factor (SCF), also referred to as the ligand for c-kit, was recently identified as a cytokine which stimulates the proliferation of progenitor cells (PCT Application No. WO 91/05795). SCF has the capacity to synergize with a wide variety of other hematopoietic growth factors to cause the proliferation and differentiation of committed progenitor cells (Migliaccio et al. *J. Cell Physiol.* 148,503 (1991)). In clonal cultures of normal mouse marrow cells, combination of G-CSF, GM-CSF or IL-3 with SCF induced up to 25 fold increase in the mean cell content and up to 6-fold increase in their mean progenitor cell content (Metcalf *Proc. Natl. Acad. Sci. USA* 88, 11310 (1991)).

Progenitor cells committed to the lymphoid lineage eventually mature to B or T lymphocytes. Mature B cells mediate humoral antibody responses by producing antibodies which circulate in the bloodstream and bind foreign antigens. The binding of antigen by antibody leads to antigen destruction by phagocytosis or by activation of complement. Antibody-producing B cells comprise a major part of the human immune response.

The involvement of growth factors in the proliferation and differentiation of hematopoietic progenitor cells to mature B cells is essential for maintaining B cell levels. The identification of such factors will be important in developing therapeutic strategies for modulating B cell levels, particularly in immunodeficient patients. One area of research is the identification of factors acting early in B cell development to stimulate the production of B cell progenitors such as pre-B cells. Pre-B cells are characterized as the early progenitor cells which express the μ heavy chain of immunoglobulin in their cytoplasm but do not express cytoplasmic light chain or surface immunoglobulin.

U.S. Pat. No. 4,965,195 disclosed that interleukin-7 (IL-7) stimulates the proliferation of pre-B cells derived from mouse bone marrow. McNiece et al. (*J. Immunol.* 146, 3785 (1991)) showed that SCF interacts synergistically with IL-7 to stimulate proliferation of B lineage cells. However, the requirement for additional factors in B cell formation has been suggested by the work of Billips et al. (*Blood* 79, 1185 (1992)). The Billips et al. reference demonstrates that pre-B cell formation from B220-, Ig-progenitor cells and expression of μ heavy chain of immunoglobulin is uniquely dependent on the presence of S17 stromal cells and can not be reproduced with IL-7, SCF, or costimulation with both IL-7 and SCF. In addition, stromal derived lymphopoietic factor-1 (SDLF-1) that alone stimulates the differentiation of B progenitor cells into pre-B cells has been described (PCT Application No. WO 89/06541).

It is therefore an object of the invention to identify factors that are involved in promoting the proliferation and differentiation of hematopoietic progenitor cells, particularly lymphoid progenitor cells, into B lineage committed cells such as pre-B cells. The factors of the invention are useful as modulators of the humoral antibody response. The therapeutic benefit of factors acting to stimulate B cell progenitors makes it desirable to identify and express the genes encoding said factors.

SUMMARY OF THE INVENTION

The present invention provides for a novel factor having the ability to stimulate the proliferation and differentiation of hematopoietic progenitor cells, specifically progenitor B cells. The factor is referred to herein as progenitor B cell stimulating factor, or PBSF. PBSF may have the amino acid sequence as set forth in SEQ ID NO. 1 and SEQ ID NO: 2. The invention also includes allelic variants, fragments and analogs of PBSF having the activity of stimulating the proliferation and differentiation of progenitor B cells. PBSF may be purified from natural sources, e.g., mammalian tissues or cell lines, or may be the product of procaryotic or eucaryotic expression of an exogenous DNA sequence, i.e., derived by recombinant means.

DNA sequences encoding biologically active PBSF are included in the present invention. Such DNA sequences include the sequence set forth in SEQ ID NO. 1 as well as allelic variants, fragments and analogs having biological activity. Also provided are vectors containing such DNA sequences and host cells transformed or transfected by such vectors. The production of the factor by the steps of growing, under suitable nutrient conditions, transformed or transfected host cells in a manner to allow expression of the polypeptide and isolating the factor is also contemplated.

PBSF is shown to stimulate the proliferation and differentiation of hematopoietic progenitor cells committed to the lymphoid lineage, such as B cell progenitors, in the presence of stem cell factor and interleukin-7.

The invention also relates to antibodies specifically binding PBSF, binding to a fusion polypeptide comprising PBSF, or to a peptide fragment containing a portion of the amino acid sequence of PBSF.

Pharmaceutical compositions comprising the factor and methods of treating hematopoietic disorders using the factor are also provided.

BRIEF DESCRIPTION OF THE FIGURES

FIG. 1 shows the nucleotide sequences encoding the signal peptidase cleavage sites of GM-CSF (SEQ ID. NO: 3), IL-1 β (SEQ. ID. NO: 5), IL-2 (SEQ. ID. NO: 4), IL-3 (SEQ ID. NO: 7) and IL-6 (SEQ. ID. NO: 6). Also shown is the sequence of the degenerate oligonucleotide probe (SEQ. ID. NO: 8) that was designed based upon the signal peptidase cleavage sites and used in screening libraries for cytokines.

FIG. 2 shows the nucleotide and deduced amino acid sequence of PBSF (SEQ. ID. NO: 1 and SEQ. ID. NO: 2).

FIGS. 5A–C show the activity of PBSF in a pre-B cell colony formation assay. PBSF is derived from conditioned medium from transfected COS cells (A), conditioned medium from transfected PA317 cells (B) or from affinity purification of conditioned medium from transfected PA317 cells (C).

DETAILED DESCRIPTION OF THE INVENTION

Figure 3:
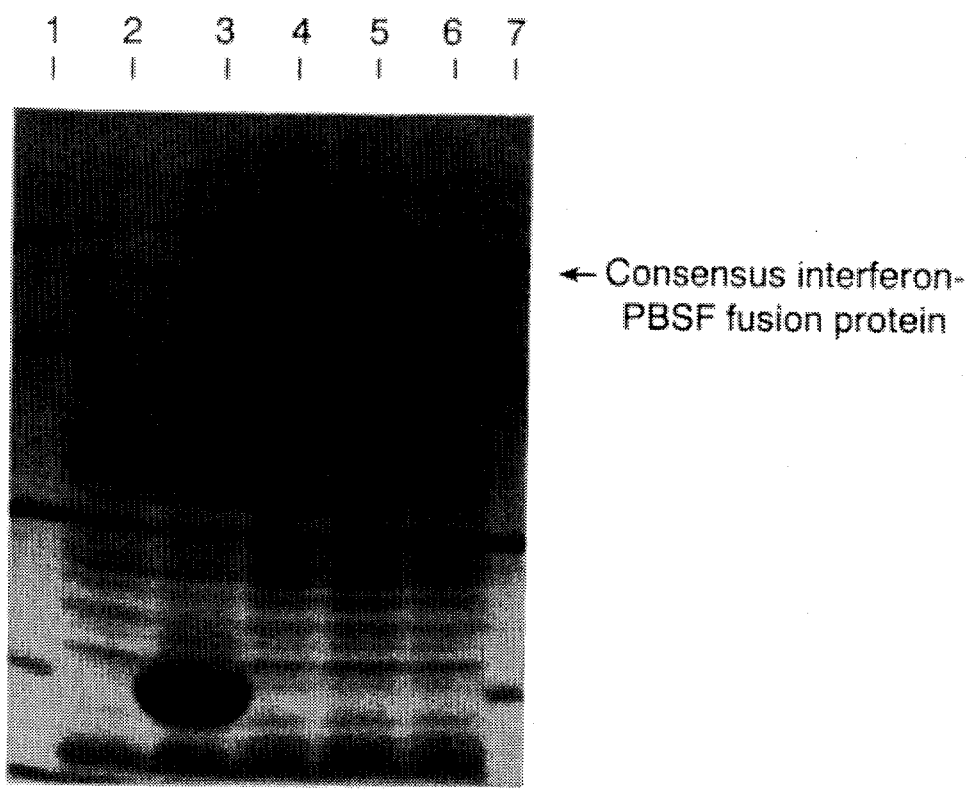
FIG. 3 shows the expression of the consensus interferon-PBSF fusion protein in E. coli. Lane 1, molecular weight markers; Lane 2, consensus interferon-PBSF fusion gene inserted in wrong orientation; Lane 3, consensus interferon gene; Lanes 4, 5 and 6, consensus interferon-PBSF fusion gene in correct orientation; Lane 7, molecular weight markers

The present invention provides for a novel factor which is a polypeptide having the ability to stimulate the proliferation and differentiation of hematopoietic progenitor cells committed to lymphoid lineage. The factor is referred to as progenitor B cell stimulating factor, or PBSF. The term progenitor B cell" is taken to mean a cell which has the capacity to give rise to mature B lymphocytes. In one embodiment, PBSF, in conjunction with IL-7 and SCF, is shown to stimulate the proliferation and differentiation of lymphoid progenitor cells to pre-B cells.

The biological activity of PBSF was determined by in vitro and in vivo assays described in Examples 5 and 6. Example 5 discloses an in vitro colony forming assay in which the number and types of colonies from 5-fluorouracil treated mouse bone marrow arising after exposure to PBSF and other growth factors is described. Example 6 discloses in vivo assays for PBSF activity involving the introduction and expression of the PBSF gene in transgenic mice, retroviral infection of baby mice with the PBSF gene and introduction and expression of the PBSF gene by mouse bone marrow transplantation.

The results from in vitro experiments (Example 5) show that PBSF stimulates the formation of B progenitor cells from mouse bone marrow cultures in the presence of SCF and IL-7. As disclosed in the specification, PBSF appears to act synergistically with SCF and IL-7 to promote the proliferation and differentiation of lymphoid progenitor cells to pre-B cells. As shown in FIG. 5, there is no stimulation of pre-B cell colony formation when either the combination of SCF and IL-7 alone or PBSF alone is added to mouse bone marrow cells. There is, however, a 50% increase in the number of pre-B cells when SCF, IL-7 and PBSF are added together to bone marrow cells in culture.

The factor of the present invention is a polypeptide that may be isolated from natural sources, e.g., mammalian tissues or cell lines which are known to be a source of cytokines or growth factors. PBSF was shown to be expressed in peripheral blood lymphocytes induced with PWM and in the human cell line Hut 78 induced with PMA (see Example 1). Alternatively, the factor may be isolated as a product of procaryotic or eucaryotic expression of an exogenous DNA sequence, i.e., derived by recombinant means.

In one embodiment, PBSF has the amino acid sequence as set out in FIG. 2 and SEQ ID NO. 1 and SEQ. ID. NO: 2. The amino acid sequence may be of the mature polypeptide or it may be of the unprocessed polypeptide. Processing of the factor to a mature protein will involve cleavage of a leader sequence, which is predicted to occur between amino acid residues 14 and 15 as shown in SEQ ID NO. 1, such that mature PBSF will have an amino terminal residue at $Thr^{15}$. Alternatively, cleavage of the leader sequence may occur between amino acid residues 31 and 32 as shown in SEQ. ID. NO. 1 and SEQ. ID. NO: 2 such that mature PBSF will have amino terminal residue at $Lys^{32}$. Other processing events could also occur, such as cleavage of one or more amino acids from either the mature amino terminus or carboxy terminus of the predicted polypeptide. Some of these processing events may convert the polypeptide to a biologically active form.

Biologically active PBSF variants are also provided. The variants include naturally occurring allelic variants, substitution analogs wherein one or more amino acids have been substituted with different amino acids, deletion analogs wherein one or more amino acids have been deleted and addition analogs wherein one or more amino acids have been added. Deletions and additions of one or more amino acids are made either within an internal region of the polypeptide or at the amino or carboxyl terminal ends. Polypeptides of the invention may also include an initial methionine residue at the amino terminal end.

Polypeptides of the invention fused to heterologous polypeptides are also provided for. In a preferred embodiment, the mature amino acid sequence of PBSF is fused at the carboxyl terminus to human alpha interferon or bovine growth hormone. The resulting fusion protein is expressed at high levels in E. coli host cells. Such fusion polypeptides are useful for the production of antibodies which specifically bind PBSF as described in Example 3. In addition, peptide fragments which are chemically synthesized may also be used to produce antibodies that bind specifically to the factor.

The present invention also provides for novel DNA sequences encoding biologically active PBSF. Preferably, the sequences comprise:

a) the DNA sequences as set out in SEQ ID NO. 1 and its complementary strand;

b) DNA sequences hybridizing to the sequences in (a); and c) DNA sequences which, but for the degeneracy of the genetic code, would hybridize to the sequences in (a) and (b). DNA sequences of the invention include those sequences coding for the mature, processed form of the polypeptide as well as for precursor forms of the polypeptide. DNA sequences coding for precursor forms of the polypeptide contain, for example, leader sequences necessary for secretion.

cDNA sequences encoding part or all of the coding region of PBSF were obtained as described in Example 1. An oligo (dT) primed cDNA library prepared from peripheral blood lymphocytes was screened by hybridization to a set of mixed oligonucleotide probes having the sequences as shown in SEQ. ID. NO. 8. The screening procedure is described in Example 1G. The probes were designed on the basis of an observed nucleotide sequence homology around the signal peptidase cleavage sites encoded by GM-CSF (SEQ ID. NO. 3), IL-1β (SEQ. ID. NO. 5), IL-2 (SEQ. ID. NO. 4), IL-3 (SEQ ID. NO. 7) and IL-6 (SEQ. ID. NO. 6) mRNAs. The rationale for this screening approach was to identify other cytokines using probes specific for the secreted portion of cytokine-like molecules. One cDNA clone which hybridized was originally designated P64 but lacked the entire coding region. Subsequently, the entire coding region of P64 was obtained on a 1.78 kb cDNA clone from a random primed peripheral blood lymphocyte cDNA library. The clone was found to have activity in stimulating pre-B cell formation and the expressed protein was referred to as PBSF. This 1.78 kb. fragment encoding PBSF was inserted into the plasmid V19.12 and transformed into *E. coli* strain DH5 alpha F' for deposit with the American Type Culture Collection (ATCC) under accession no. 69133 on Nov. 25, 1992. Because of the high degeneracy of the probe mixture (about 65,000 fold), positively hybridizing clones were obtained which had sequences similar to the signal peptidase cleavage site in other regions of the molecule. This was the case with the gene encoding PBSF.

DNA sequences of the invention may be cDNA and genomic DNA sequences isolated from human and other mammalian sources. Also contemplated are synthetic DNA sequences encoding PBSF, and fragments thereof, which are readily produced by gene synthesis techniques well known in the art. DNA sequences encoding PBSF disclosed in the present application, and fragments thereof, may be used as probes to isolate genomic DNA encoding PBSF. In addition, DNA sequences containing part or all of the PBSF gene are useful in detecting the presence of the gene in biological samples, in mapping the position of the gene on the human chromosome, and in nucleic acid-based therapeutics, such as anti-sense or triple helix blocking, where it is desirable to regulate the quantities of PBSF that are synthesized.

The DNA sequences also include sequences coding for biologically active PBSF variants. The sequences include those coding for naturally occurring allelic variants, substitution analogs, deletion analogs and addition analogs, wherein the deletions and additions may be introduced at the amino or carboxyl terminus or within the coding region. Techniques that are well known in the art are employed to construct such analogs. Such variants may have a number of desirable properties, e.g., more resistant to proteolysis, more resistant to oxidation, or more easily refolded upon expression in microbial hosts, while still retaining biological activity.

DNA sequences include those coding for fusion proteins, wherein part or all of the DNA sequence of PBSF is fused to a heterologous protein. Preferably, DNA sequences coding for part of human consensus interferon or bovine growth hormone are fused in frame to the 5' end of the DNA sequence encoding PBSF. The construction of fusion proteins is described in Example 3A. As shown in Example 3B, such fusion proteins are useful for the production of antibodies to the factor.

PBSF is characterized by being the product of procaryotic or eucaryotic host expression (e.g., by bacterial, yeast, plant, insect and mammalian cells in culture) of exogenous DNA sequences, wherein the exogenous DNA sequences may be cDNA, genomic DNA or synthetic DNA. That is, in a preferred embodiment, the factor is derived by recombinant means. As hematopoietic growth factors are generally produced in only small quantities by natural sources, the ability to produce the factor by recombinant methods is essential to obtaining quantities sufficient for therapeutic applications.

A variety of vectors are readily available for the expression of DNA sequences encoding PBSF in host cells. Vectors such as V19.12, pDSRα2 and mpZen have been described in Examples 2A–C for the expression of PBSF in COS, Chinese Hamster Ovary (CHO) and PA317 mammalian cell lines, respectively. In addition, PBSF may be expressed in a number of vectors suitable for use in yeast and bacterial strains. As described in Example 2, PBSF was expressed as a fusion protein with either human alpha interferon or bovine growth hormone sequences in *E. coli* using the vector pCFM 756. PBSF sequences may be optimized for expression in a particular host system, whether it be a bacterial, yeast, or mammalian host cell. Such optimization may involve the inclusion of preferred codons for expression. In one preferred embodiment, the PBSF sequences include one or more codons optimized for expression in *E. coli* host cells. Also provided for are vectors for the expression of PBSF in transgenic mice as described in Example 4A.

A process for the production of recombinant PBSF is also described. The process comprises growing, under suitable nutrient conditions, procaryotic or eucaryotic host cells transformed or transfected with a DNA sequence encoding biologically active PBSF and isolating PBSF expressed by said DNA sequence. Preferably, the sequence is that set forth in SEQ ID NO. 1 and sequences hybridizing thereto.

Depending upon the host cell used for expression, the polypeptide of the invention may be glycosylated or nonglycosylated. Mammalian proteins are usually modified by the attachment of carbohydrate chains at specific locations along the amino acid backbone. Attachment of carbohydrate chains at selected asparagine residues is termed N-glycosylation while carbohydrate at serine or threonine residues is termed O-glycosylation. The presence of either N-linked or O-linked chains, or both, may be required for biological activity and/or stability of the polypeptide. The existence of N-linked glycosylation sites can be predicted by the sequence Asn-X-Ser/Thr where X can be any amino acid. Based upon this, PBSF is predicted to have two N-linked glycosylation sites at $Asn^{29}$ and $Asn^{396}$.

The PBSF polypeptide may also be modified with a water soluble polymer such as polyethylene glycol. Covalent attachment of water soluble polymers to proteins is carried out using techniques known to those skilled in the art and have been described in U.S. Pat. No. 4,179,937, hereby incorporated by reference. The modified polypeptide may have desirable properties such as increased solubility in aqueous solutions, increased stability, longer in vivo half-life and increased biological activity.

PBSF may also be covalently attached to a detectable label which may be radioactive (e.g., $I^{125}$) or nonradioactive (e.g., a fluorescent dye). The attachment of a reporter group provides reagents useful for the detection of PBSF in solid tissues and fluid samples. Similarly, DNA sequences encoding PBSF may be covalently attached to detectable labels for use as probes for PBSF sequences in biological samples, for example, in mapping the location of the human PBSF gene in the genome and for detecting the presence of PBSF related sequences.

Antibodies specifically binding the factor are also comprehended by the invention. The antibodies may be monoclonal or polyclonal and may bind specifically to polypeptide fragments and fusion polypeptides as well as to the intact protein. The production of antibodies to a human consensus interferon-PBSF fusion protein and a bovine growth hormone-PBSF fusion protein is described in Example 3B. Antibodies are useful in quantitating the amount of factor in biological samples (e.g., blood or urine). Abnormal concentrations of the factor may be a useful indicator of certain hematopoietic disorders. Further, antibodies specifically binding PBSF are useful in a method for the purification of the polypeptide, either from natural sources or from expression of recombinant plasmids, wherein the method comprises the steps of:

a) attaching an antibody to a solid support, b) contacting said attached antibody with a solution containing the polypeptide in such a manner as to selectively bind the polypeptide to the antibody; and c) eluting the bound polypeptide. The solution containing the polypeptide may be a crude or partially purified mixture. The purification of PBSF using an anti-PBSF antibody affinity column is described in Example 5.

The invention provides for pharmaceutical compositions comprising therapeutically effective amounts of PBSF together with pharmaceutically acceptable diluents, adjuvants, carriers, preservatives, emulsifiers and/or solubilizers. A "therapeutically effective amount" as used herein refers to that amount which provides therapeutic effect for a given condition and administration regiment. It is expected that one skilled in the art would be able to determine a therapeutically effective amount of PBSF for any given condition being treated. Pharmaceutical compositions include diluents of various buffers (e.g., Tris, acetate, phosphate), solubilizers (e.g., Tween, Polysorbate), carriers such as human serum albumin, preservatives (thimerosal, benzyl alcohol) and anti-oxidants such as ascorbic acid. The factor may also be incorporated into particulate preparations of polymeric compounds for controlled delivery to a patient over an extended period of time. A more extensive survey of components in pharmaceutical compositions is found in Remington's *Pharmaceutical Sciences,* 18th ed. A. R. Gennaro, ed., Mack, Easton, Pa. (1990).

Dosage of PBSF used to treat hematopoietic disorders will vary depending upon a number of factors, including the nature and severity of the disorder being treated, the route of administration, the use of PBSF in combination with other therapy. Also to be considered is the in vivo half-life of the PBSF polypeptide or a modified form thereof wherein the modification can be with a water soluble polymer such as polyethylene glycol. A "therapeutically effective amount" of PBSF as used herein can be determined by one skilled in the art taking into account these factors.

PBSF may be administered by injection, either subcutaneous, intravenous or intramuscular, or by oral or nasal administration. The route of administration will depend upon the particular condition being treated.

PBSF is used alone or in combination with other therapy in the treatment of a number of hematopoietic disorders. In a preferred embodiment, PBSF is used in combination with SCF and IL-7 for the treatment of B cell disorders. The factor may also be used with other factors known to be involved in various stages of hematopoiesis such as IL-1, IL-2, IL-3, IL-4, IL-5, IL-6, low molecular weight B cell growth factor (L-BCGF), or high molecular weight B cell growth factor (H-BCGF) for the treatment of B cell disorders. Administration of other hematopoietic factors may be concurrent with, prior to, or after administration of PBSF.

PBSF may be used alone or in conjunction with other factors to treat a number of hematopoietic disorders that result from disease or injury to bone marrow. These disorders include the following: cytopenia, aplastic anemia, myelodysplastic syndrome, leukemic disease, and stem cell transplantation. In addition, marrow injury resulting from radiation treatments or chemotherapy leads to myelosuppression which may be overcome by treatments with the factor. In a preferred embodiment, PBSF is administered in conjunction with SCF and IL-7 for the treatment of B cell disorders, particularly those disorders involving decreased levels of B cells. A deficiency in B lymphocytes leads to a depressed immune response and a greater susceptibility to disease. PBSF is advantageously administered to an immunocompromised patient.

PBSF will be useful in expanding B progenitor cells in bone marrow prior to syngeneic, allogeneic or autologous bone marrow transplantation. The factor may be administered directly to patients to increase the production of B progenitor cells in the marrow or administered ex vivo to marrow cultures prior to transplantation. It is expected that such treatment will reduce the period of depressed immunity experienced by patients after transplantation.

The following examples are offered to more fully illustrate the invention, but are not to be construed as limiting the scope thereof.

EXAMPLE 1

Identification of a cDNA Clone (P64) Encoding PBSF

A. Isolation of lymphocytes

Peripheral blood lymphocytes were isolated from freshly prepared buffy coats obtained from Hemacare (Sherman Oaks, Calif.): Buffy coats were diluted three times with phosphate buffered saline (PBS). 30 ml of the diluted buffy coats were pipetted into 50 ml culture tubes (Fisher Scientific, Pittsburgh, Pa.) and underlaid with 10 ml of Ficoll-Paque (Pharmacia, Piscataway, N.J.). After centrifugation at 3200×g, the mononuclear cells present in the interphase were removed and washed three times in 30 ml each of PBS. The pellet was then suspended in 50 ml of RPMI 1640 and 10% fetal bovine serum (FBS), diluted 50 fold and cell number determined.

B. Induction of Cytokine Expression

About $5 \times 10^6$ cells/ml were incubated with poke weed mitogen (PWM; 10 µg/ml. Sigma, St. Louis, Mo.) for 19 hours followed by addition of cycloheximide (Sigma) to 10 µg/ml for an additional 6 hours. For comparison, the same amount of cells were incubated with or without PWM for the same time period. Incubation was carried out at 37° C. and 5% $CO_2$.

C. Isolation of RNA

Total RNA from induced peripheral blood lymphocytes was isolated using the guanidinium thiocyanate technique (Chirgwin et al. *Biochemistry*, 18, 5294 (1979)). Briefly, cells were collected by centrifugation and lysed in a solution of 4M guanidinium thiocyanate containing 4% mercaptoethanol. Adherent cells were lysed in the same solution and pooled. After three passages through an 18 gauge needle, the lysate was overlaid on a step gradient of 5.7M cesium chloride. Centrifugation at 76,000×g was carried out in a Beckman L2 ultra centrifuge for 24 hours at 20° C. After centrifugation, pelleted RNA was suspended in 10 mM Tris, 1 mM EDTA, pH 7.5 plus 0.1% SDS and precipitated by the addition of 2.5 volumes of 100% ethanol and sodium acetate (pH 5.0) to 0.3M.

D. Selection of poly (A)+ RNA poly (A)+ RNA was selected by chromatography on oligo (dT) -cellulose (Collaborative Research, Bedford, Mass.) using procedures described in Maniatis et al. (*Molecular Cloning, A Laboratory Manual*, 1st ed. Cold Spring Harbor Laboratory, Cold Spring Harbor, N.Y. (1982)), ethanol precipitated, and centrifuged. The final pellet was dissolved in distilled water and stored in liquid nitrogen in aliquots.

E. cDNA library construction

About 5 µg of polyA+ RNA in 10 µl was denatured with 10 mM methyl mercury hydroxide at room temperature for 10 min, followed by the addition of β-mercaptoethanol to 10 mM and RNasin (Promega, Madison, Wis.) to 3 u/µl and incubation at room temperature for 5 min. The following components were then added to the indicated final concentrations: 50 µg/ml oligo(dT), 2 mM dNTP (Pharmacia), 100 µg/ml. bovine serum albumin, first strand buffer (50 mM Tris-HCl, pH 8.6, 75 mM KCl, 10 mM $MgCl_2$, Bethesda Research Laboratories, Gaithersburg, Md.) and 20 u/µl Superscript reverse transcriptase (BRL). First strand synthesis was allowed to proceed at 37° C. for one hour. The mixture was then diluted with the second strand buffer (20 mM Tris-HCl, pH 7.5, 5 mM $MgCl_2$, 100 mM KCl, 50 µg/ml. bovine serum albumin, 10 mM dithiothreitol, BRL), 0.125 u/µl. *E. coli* DNA polymerase I (BRL), 0.08 u/µl Rnase H (BRL), 0.1 u/µl *E. coli* DNA ligase (New England Biolabs, Beverly, Mass.) and 0.15 mM NADP (Sigma). All concentrations stated are those in the reaction mixture. The mixture was incubated at 15° C. for 1 hour followed by one hour at 25° C. T4 DNA polymerase (Pharmacia) was then added to 0.01 u/µl and the reaction incubated at 37° C. for 30 min. to generate blunt ends. Unincorporated dNTPS were removed by two ethanol precipitations in the presence of 2M ammonium acetate.

The double-stranded cDNA was then methylated with Eco RI and Alu I methylases (Boehringer Mannheim, Indianapolis, Ind.) according to the following procedure. To double-stranded cDNA in water was added methylation buffer, 100 uM S-adenosyl methionine, and 1 u/µl of Alu I methylase and incubated at 37° C. for one hour. Then NaCl was added to 0.1M and EcoRI methylase added to 10 u/µl. The reaction was incubated at 37° C. for 30 min.

The oligo-adaptor having the sequence 5' GCT TGA ATT CAA GC 3' (see SEQ ID. NO. 9) was ligated to the cDNA overnight. cDNA was electrophoresed on a 0.8% agarose gel and molecules longer than 500 bps. were electro-eluted from the gel. The eluted cDNA was extracted with a 1:1 mixture of phenol/chloroform, precipitated with ethanol, suspended in water and digested sequentially with Hind III and Eco RI restriction enzymes to generate Eco RI cohesive ends on the 5' end of the molecules and Hind III cohesive ends on the 3' end of the molecules.

A 592 bp. Aat II/Cla I fragment containing the origin of replication from bacteriophage M13 was inserted into the eucaryotic expression V19.8, which was described in PCT Application No. WO 91/05795, to generate the vector V19.10. V19.10 was digested with Eco RI and Hind III and treated with bacterial alkaline phosphatase. Ligation reactions were set up at different ratios of cDNA to vector DNA and the ratio giving rise to the highest number of clones after transfection was chosen for large scale ligation. Competent DH5 α F' *E. coli* cells (Gibco-BRL) were used for transfection. The library was plated on 15 150 mm plates which were then scraped in the presence of SOB (Okayama et al. *Methods in Enzymol.* 154, 3 (1987)) and stored in 7% DMSO at −80° C.

An additional cDNA library was constructed from polyA selected RNA isolated from peripheral blood lymphocytes in which a random hexamer primer (Pharmacia) was used to prime the first strand cDNA synthesis. Double stranded flush-ended cDNA was generated as described above for the oligo dT primed library. An adaptor (In Vitrogen, San Diego, Calif., catalog no. N408-8) having the sequence as in SEQ. ID NO. 10: and SEQ. ID. NO: 11.

```
5' CTTTCCAGACACA 3'
   GAAAGGTC
``` was ligated to the cDNA. V19.12 was constructed by inserting the Hind III/NotI stuffer fragment of pCDM8 (In Vitrogen) between the Hind III and Not I sites of V19.10. V19.12 was digested with Bst XI restriction enzyme and then ligated to the cDNA. Transformation of *E. coli* DH5 α F' host cells and storage of the cells was performed as described above.

F. Probe Design

Mixed oligonucleotide probes were designed on the basis of some sequence homology around the signal peptidase cleavage site of a few cytokines. The probes were designed as shown in FIG. 1 using the published sequences from GM-CSF, IL-1, IL-2, IL-3 and IL-6 encoding signal peptidase cleavage sites (Wong et al. Science 228, 810 (1985); Nishida et al. *Biochem. Biophys, Res. Comm.* 143, 345

(1987); Taniguchi et al. *Nature* 302, 305 (1983); Yang et al. *Cell* 47, 370 (1986); and May et al. *Proc. Natl. Acad. Sci.* 83, 8957 (1986)). The degeneracy of the probe mixture was 65,536. Due to the high degeneracy, it was possible to isolate clones which have similar sequences in regions other than the signal peptidase cleavage site.

G. Screening of cDNA Libraries

High density screening of the oligo(dT) primed peripheral blood lymphocyte library in DH5α F' *E. coli* was carried out by plating about 10,000 colonies per 150 mm plate on a GENE SCREEN PLUS membrane (New England Nuclear/DuPont, Boston, Mass.). A replica onto a second gene screen membrane was made and the colonies on the replica plate were allowed to grow overnight on an LB plate containing the drug 100 µg/ml ampicillin. The replica membranes were then placed on an LB plate containing 100 µg/ml chloramphenicol for amplification of plasmid DNA. After overnight amplification, DNA in the colonies were denatured in 0.5N NaOH and 1.5M NaCl for 5 minutes, followed by renaturation in 1M Tris-HCl pH 7.5. The membranes were air dried and baked for 2 hours at 80 C. in vacuum. Filters were wet in 2×SSC, followed by two 30 min. prewashes in 6×SSC, 0.2% SDS. Prehybridization was carried out in 6×SSC, 5×Denhardt, 0.1% SDS for 4–5 hours. 20 pmoles of mixed oligonucleotide probe was labelled with $\gamma p^{32}$-ATP using T4 polynucleotide kinase and the unincorporated label was removed by centrifugation through a Sephadex G-50 column. About $2\times10^6$ cpm per ml was used in hybridization at 55° C. in 6×SSC, 0.1% SDS and 5×Denhardt's solution. After 20 hours the filters were washed 30 minutes twice at 55° C. in 6×SSC and 0.1% SDS. An additional wash was carried out at the same temperature in 2×SSC plus 0.1% SDS. After overnight exposure, the areas in the master plate corresponding to the positive signal area were scraped and suspended in SOB. Serial dilution of the colonies were plated on ampicillin plates for secondary screening. Individual colonies were identified and grown up overnight for isolation of plasmid DNA. A final screening was carried out by hybridizing the oligonucleotide probe to plasmid DNA from different colonies. About 80 positive clones were identified in this manner.

Plasmid DNA from positive clones were sequenced on both strands using primers hybridizing to sequences in the 19.10 vector that are 5' and 3' to the cDNA inserts. DNA sequencing of cDNA clones was carried out as described in Sanger et al. *Proc. Natl. Acad. Sci.* 74, 5463 (1977). The DNA sequence was compared to those present in various versions of the GenBank sequence database. Only those sequences not appearing in GenBank were further characterized by obtaining sequences of the full length clones and analyzing the sequences using the Genetics Computer Group (University of Wisconsin) software package. One of the clones that was pursued further was designated P64.

The P64 clone isolated from the oligo dT primed peripheral blood lymphocyte cDNA library lacked the 5' end of the gene as indicated by an absence of the initiator methionine residue. In order to obtain a full-length clone of P64, a PMA activated Hut78 λ gt11 cDNA library from Clontech Laboratories (Palo Alto, Calif. Catalog No. HL 1068b) was probed with the P64 cDNA clone. About 10,000–20,000 plaques per 150 mm plate were replica plated onto Gene Screen filters and probed with the P64 clone labelled with $^{32}p$ by the random priming method. After secondary screening, individual positive colonies were identified. The insert was released by digestion of the positive lambda cDNA clones with Eco RI and subcloned into the Bluescript SK II plasmid (Stratagene, La Jolla, Calif.) and sequenced. This clone contained upstream coding sequences, but the initiator methionine codon was still lacking.

In another attempt to obtain a full-length P64 clone, a random primed peripheral blood lymphocyte cDNA library in V19.12 was screened using the P64 cDNA clone isolated from the Hut78 library as a probe. Multiple positively hybridizing clones were obtained and the DNA inserts were subcloned into M13 mp21 and sequenced. Several clones had coding regions identical to the Hut 78 clone and in addition contained sequence coding for the initiator methionine residue. One isolate contained an insert of approximately 1780 bps. having the entire coding region of P64. This clone encodes the polypeptide designated as progenitor B cell stimulating factor or PBSF.

This 1.78 kb DNA fragment inserted into the plasmid V19.12 and transformed into *E. coli* strain DH5α F' has been deposited with the American Type Culture Collection (ATCC) under accession number 69133 on Nov. 25, 1992.

H. DNA Sequencing and Analysis

GenBank, EMBL and Swiss Prot databases were searched to find sequences identical to or highly homologous with PBSF sequences at the nucleic acid and amino acid levels. The search was carried out using FastA and TfastA programs of the GCG Software Package. Analysis of the nucleic acid structure was carried out using Map and Translate programs. The amino acid sequence of PBSF was analyzed by the use of Pepplot, Pepstructure, Motifs and Isoelectric programs. Sigseq1 program was used to predict the signal peptide cleavage site. Multiple searches of the GenBank EMBL database were performed to compare the PBSF sequence with those present in the database. None of the searches revealed a high degree of homology between PBSF and sequences in the database.

I. The PBSF Gene and the Encoded Protein

The DNA sequence of P64 as deduced from cDNA clones obtained from the hut 78 library and from the oligo dT primed and random primed PBL libraries is shown in FIG. 2 and SEQ. ID. NO. 1. The sequence extends for 2376 bps. The size of the P64 protein deduced from the DNA sequence is about 52 kDa, comprising of 491 amino acids including the leader sequence. The signal peptide cleavage site is predicted to be between amino acid residues alanine at position 14 and threonine at position 15 in SEQ. ID. NO. 1 and SEQ. ID. NO: 2 as described in von Heinje (*Nuc. Acid Res.* 14, 4683 (1986)). There is also a probability of cleavage between serine at position 31 and lysine at position 32. There is a long 3' untranslated region, containing multiple TATT and TTTT motifs, which are present in a number of cytokine molecules (Shaw et al. *Cell* 49, 659 (1986)). The predicted protein has a hydrophobic amino terminus. There are six cysteine residues. The isoelectric point is 7.25 as predicted by the program ISOELECTRIC in the GCG software package. There are two potential N-linked glycosylation sites at $Asn^{29}$ and $Asn^{396}$. In addition, there are four potential protein kinase C phosphorylation sites and five creatine kinase II phosphorylation sites.

EXAMPLE 2

Expression of Recombinant PBSF Protein

A. Expression in Cos cells

Cos cells were transfected with V19.12 DNA containing the 1.78 kb PBSF cDNA insert by electroporation. About $3\times10^6$ cells in PBS were electroporated using the electro cell manipulator 600 (BTX, San Diego, Calif.) at 500 volts/capacitance and resistance, capacitance at 1000 µF, resistance of 48 ohms at a charging voltage of 150 volts in a volume of 400 µl using a cuvette of 2 mm gap. The pulse length was from 8.3 to 10.5 msec. The cuvette was kept on ice for five min. followed by dilution in DMEM containing 10% fetal bovine serum and plating in a 10 cm. plate. After overnight incubation at 37° C., 5% $CO_2$, media was changed to eliminate dead cells. Serum-free DMEM was added to the plate and conditioned medium (CM) was harvested after 72 hours for bioassays. The CM was filter sterilized and frozen in aliquots at −20° C. The presence of P64 protein in the medium was detected by Western blot analysis using antibodies generated against a P64 fusion protein as described below.

B. Expression in Chinese hamster ovary (CHO) cells

CHO cells constitutively producing PBSF were generated as follows. CHO (DHFR⁻) cells were transfected with the vector pDSRα2 (PCT Application No. WO 91/05795) containing the PBSF coding region. The following primers were used in PCR to amplify the PBSF coding region:

5' TGTCCTCCGGCCCGAGATGA (Nucleotides 12–31 in SEQ ID NO. 1); and
5' GGTTTGTGTTTTATGATACATTAC (Nucleotides 1567–1590 in SEQ. ID NO. 1)

The amplified DNA was digested with Hind III and Sal I and cloned into pDSRα2. After initial selection of transfectants in a medium containing dialyzed serum, the cells were further selected in the presence of increasing concentrations of methotrexate up to 1 µM for plasmid amplification. Selected colonies were checked for the expression of the PBSF gene by dot Northern hybridization. Conditioned medium for bioassays was generated by growing CHO(DHFR⁻) cells in serum-free DMEM for 72 hrs.

C. Expression in PA317 cells

The 1.78 kb. Hind III fragment encoding PBSF was inserted into the mpZen vector (Johnson *Dev. Biol. Stand.* 69, 3 (1988)) for the expression of PBSF under the myeloproliferative sarcoma virus (MPSV) promoter. Psi 2 cells (Miller et al. *Biotechnique* 7, 980–990 (1989)) were transfected by electroporation with mpZen containing the PBSF gene along with the plasmid SV2-Neo. Neomycin-resistant colonies were selected on G418 and RNA was dot blotted and hybridized to identify those colonies producing high levels of PBSF. Conditioned medium from a high level producer was used to infect the amphitrophic packaging cell line PA317 (Miller et al. *Mol. Cell. Biol.* 6, 2895–2902 (1986)) in the presence of polybrene. Conditioned medium was generated from transfected PA317 cultures for bioassays and for infections of baby mice (see below). These cells were also used for bone marrow transplantation experiments.

EXAMPLE 3

Expression of PBSF Fusion Protein and Production of Antibodies

A. *E. coli* fusion protein

The hut 78-derived cDNA clone for PBSF was used to produce a fusion protein with either human consensus interferon or bovine growth hormone. A DNA fragment containing either the first 80 amino acids of human consensus interferon or the first 108 amino acids of bovine growth hormone was fused in frame to the P64 coding region at the $Asn^2$ residue. The consensus interferon-PBSF or bovine growth hormone-PBSF fusion proteins were expressed from the $p_L$ promoter of the plasmid pCFM 756, a modified version of pCFM736 (pCFM 736 is described in U.S. Pat. No. 4,710,473). *E. coli* FM5 was transfected with the gene encoding the fusion protein and grown at 28° C. until the OD600 was 0.3 to 0.5. The temperature was then increased to 42° C. for 2–3 hours. Emergence of inclusion bodies were visualized by light microscopy. *E. coli* cells were then lysed in Laemmli buffer and analyzed by SDS-PAGE on a 10% gel. Protein bands were visualized by Coomassie blue staining. The expression of the consensus interferon-PBSF fusion protein is shown in FIG. 3.

B. Antibody production

*E. coli* producing either a consensus interferon-PBSF or bovine growth hormone-PBSF fusion protein was grown and induced in a 500 ml batch as described above. After centrifugation, the pelleted cells were suspended in chilled water and broken by passing three times through French press at 7500 psi. After centrifugation the pelleted inclusion bodies were extracted with 5M urea to reduce the contamination of *E. coli* proteins. Fusion proteins were isolated from polyacrylamide gels as described (Hunkapiller M. et al, *Methods in Enzymol.* 91, 227–236). The gel isolated fusion proteins were lyophilized and injected to rabbits to raise antibodies. Alternatively, a PBSF peptide fragment (Cys-Arg-Glu-Lys-Lys-Thr-Glu-Asn-Ser-Lys-Leu-Arg-Lys-Val-Lys-Tyr) as set forth in SEQ ID NO. 12 was synthesized, conjugated to keyhole limpet hemocyanin (CalBiochem, La Jolla, Calif., Catalog No. 374811) and injected into rabbits to raise antibody (Liu et al. *Biochem.* 18, 690–697 (1979)).

EXAMPLE 4

Purification of PBSF

A. Purification of Rabbit Anti-PBSF antibodies and Immobilization on Cyanogen Bromide-Activated Sepharose.

Crude rabbit antibodies against the bovine growth hormone-PBSF fusion protein were purified on a Affi-gel Protein A agarose column (Bio-Rad, Richmond, Calif., Catalog No. 153-6153) using a procedure published by the manufacturer with the Affi-gel Protein A MAPS kit. The purified antibodies were coupled to cyanogen bromide activated sepharose using a procedure published as part of the IMMUNOPURE Antigen/Antibody Immobilization Kit (Pierce, Rockford, Ill., Catalog No. 44890).

B. Purification of PBSF

Figure 4:
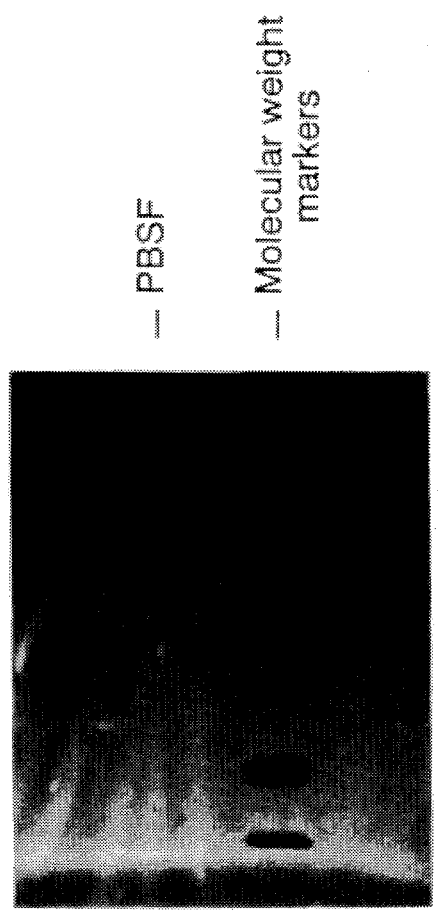
FIG. 4 shows SDS-PAGE of PBSF expressed in PA317 cells and affinity purified by immobilized anti-PBSF antibody.

Conditioned medium from PA317 cells transfected with mpZEN-PBSF was the source of PBSF. The procedures used for applying sample to the antibody column and eluting PBSF from the column are those described in the IMMUNOPURE kit. After elution from the column, purified PBSF was dialyzed against PBS and was analyzed by SDS-PAGE and silver staining of the 10% gel. The results are shown in FIG. 4.

EXAMPLE 5

In Vitro Biological Activity of PBSF

Colony forming assays

Bone marrow cells obtained from normal adult Balb/c mice or mice treated previously with 5-fluorouracil (5-FU)

were plated in double layer agar cultures in 35-mm dishes as previously described (Bradley et al. *J. Cell Physiol.* 94, 507 (1978)). α-modification of Eagle's MEM (Flow Labs, McLean, Va.) supplemented with 20% fetal calf serum was used for all cultures. Growth factors (SCF, IL-7 and PBSF) were incorporated in the underlays at a maximum of 13.2% of the total culture volume (1.5 ml per dish). Cultures were gassed with a 5% $O_2$,: 10% $CO_2$: 85% $N_2$ mixture and incubated for 10 to 14 days. Only colonies containing 50 or more cells were scored.

Figure 5A:
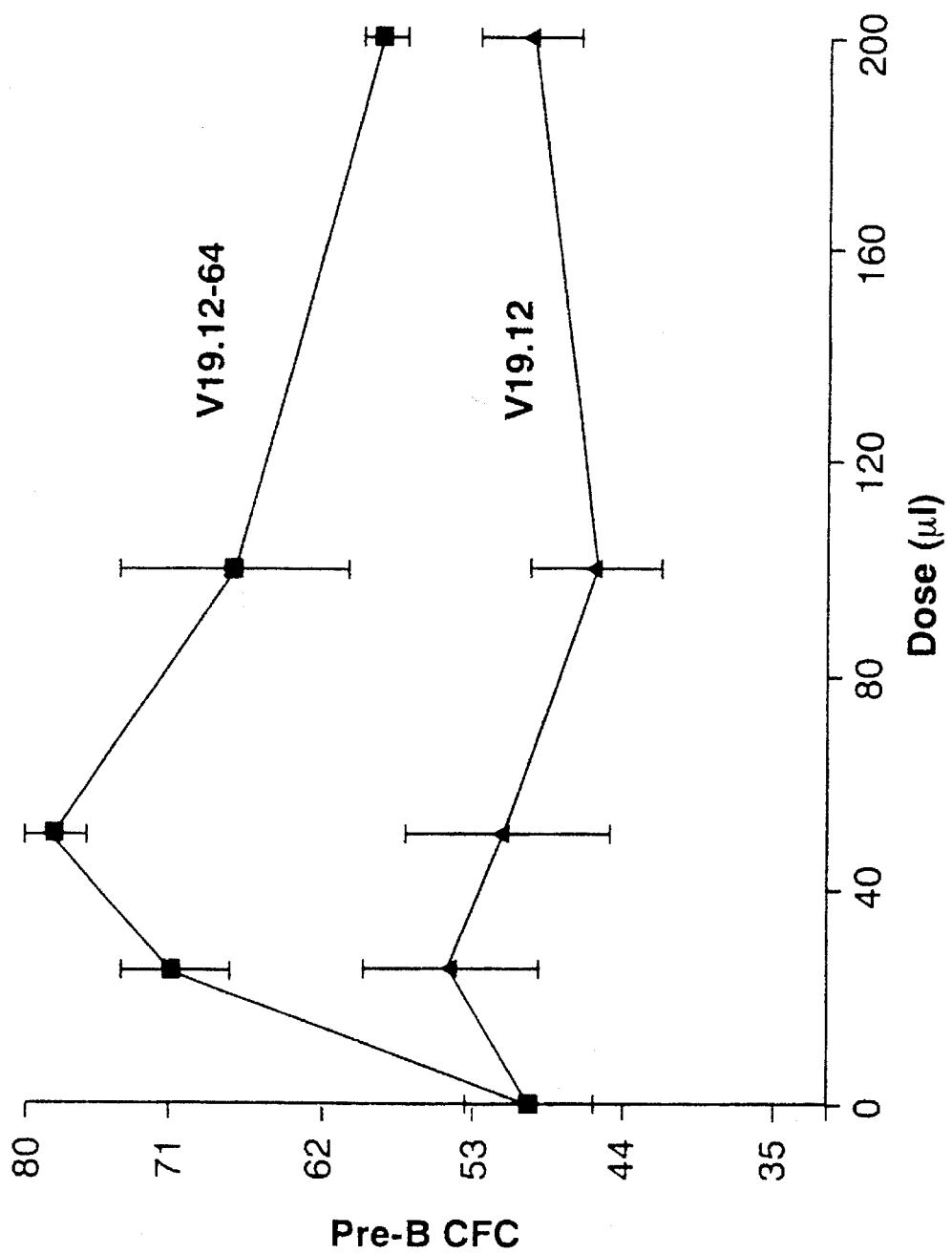
Figure 5C:
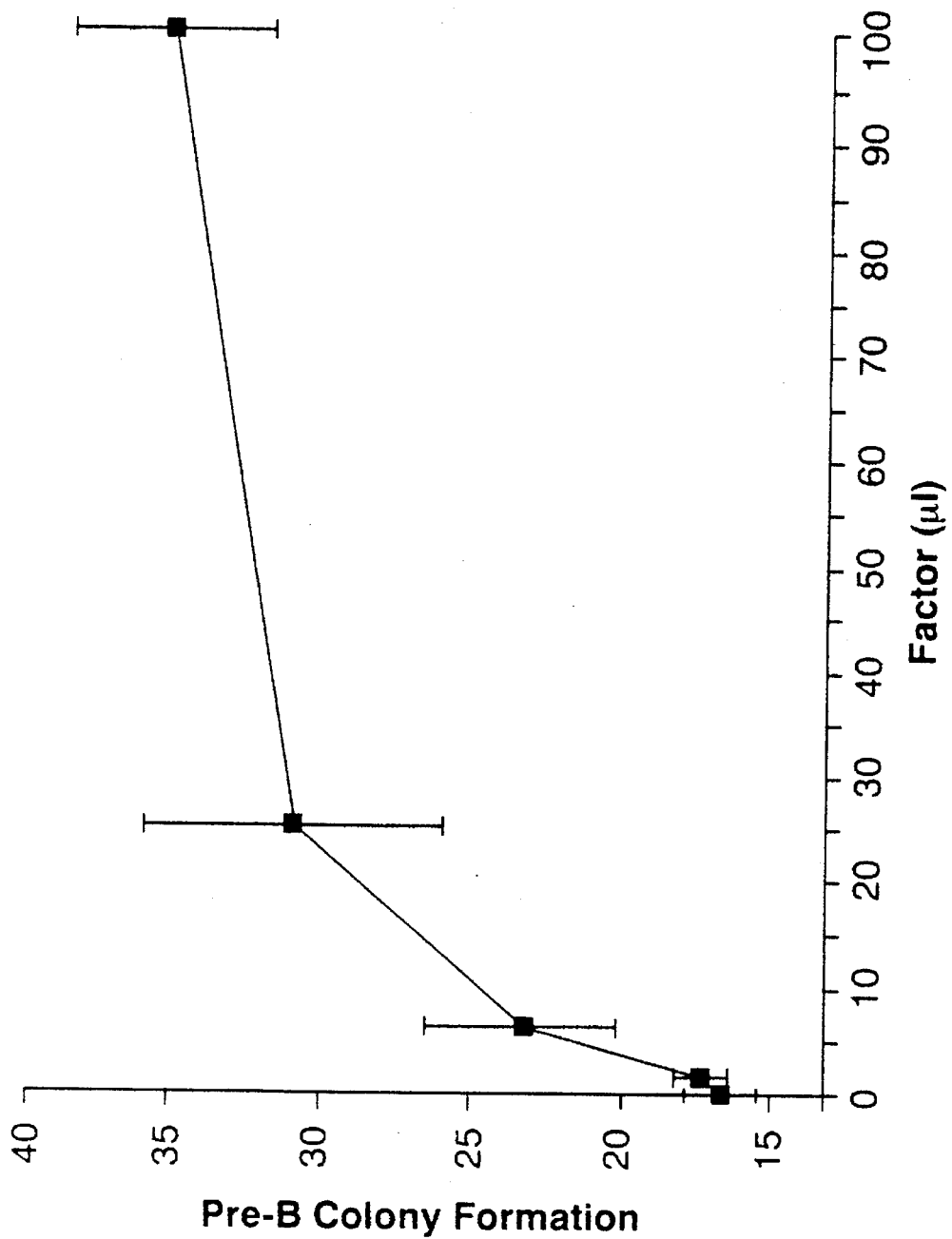

All colony forming assays were done in the presence of recombinant rat stem cell factor of 164 amino acids in length (rrSCF164) expressed in *E. coli* and purified as described in Martin et al. Cell 63, 203 (1990) and recombinant human IL-7 (Biosource International, Westlake, Calif.). rrSCF164 and recombinant human IL-7 were each added to a final concentration of 200 ngs/ml of culture. In FIG. 5A, assays were done to compare pre-B cell formation stimulated by conditioned medium from Cos cells transfected with either the vector 19.12 or 19.12 containing the 1.78 kb PBSF DNA fragment. In FIG. 5B, assays were done to measure pre-B cell formation by conditioned medium generated from PA317 cells carrying the PBSF gene in a retroviral vector, pZen. In FIG. 5C, purified PBSF prepared as described in Example 4 and added to bone marrow cells at the indicated volumes. The appearance of pre-B cells was verified by demonstrating that the colonies formed expressed B220 Ag and cytoplasmic μ chain but did not express surface Ig.

EXAMPLE 6

In Vivo Biological Activity of PBSF

A. Transgenic Mice

The 1.78 kb Hind III fragment carrying the PBSF gene was cloned into V19.13 which is similar to V19.12 but contains the rat albumin promoter in place of SV 40 early promoter. The DNA fragment was inserted 3' to the rat albumin promoter and enhancer. The coding sequence of the PBSF cDNA containing the albumin promoter was purified by banding on CsCl, dialyzed against 1× injection buffer (Injection buffer is 10 mM Tris, 0.1 mM EDTA, pH 7.5). 1-2 ng/μl of DNA (equivalent to about 500 copies of the linear DNA molecule) was injected per egg. The injected eggs were implanted into the pseudopregnant mice and offspring appeared 20 days later. The presence of PBSF DNA sequences in the founders was determined by PCR amplification of the DNA isolated from the tails. Blood collected from the tail bleed was analyzed on Sysmex to enumerate the white blood cell, red blood cell and platelet populations.

Founders were then inbred to generate the F1 animals, which were screened for the presence of PBSF gene. RNA isolated from the livers, bone marrow, spleen and muscle of the F1 mice were screened by reverse transcription and PCR to detect the expression of PBSF.

In order to characterize the systemic effect of PBSF expression, different organs of the F1 were isolated, fixed and cut into thin sections for histochemical analyses.

B. Retroviral Infection of Baby Mice 3 to 4 day old baby Balb/C mice were injected i.m. with 50 μl of a mixture of conditioned medium from PA317 cells transfected with either the mpZen vector, mpZen vector containing the gene encoding G-CSF, or mpZen containing the PBSF gene, and conditioned medium from NIH 3T3 cells infected with wild Moloney virus. PA317 conditioned medium and 3T3 conditioned medium were present in a ratio of 10:1 (v/v), respectively. Blood was collected in EDTA coated microfuge tubes from tail vein after intervals of 1, 2, and 3 months. Blood smear was prepared for Giemsa staining and differential counting. Sysmex analysis of the blood was carried out to enumerate the white blood cell, red blood cell and platelet population. Up on death or after euthanization, selected vital organs were removed for histological analysis.

C. Bone marrow gene transfer

B57/J mice were irradiated to destroy bone marrow cells. These mice were then transplanted with bone marrow cells from donor animals after infection in vitro by coculture for 5 days with PA317 cells harboring either the mpZen vector alone of the vector containing G-CSF or PBSF genes. After survival confirmed the successful transplantation, RNA was isolated from the blood and analyzed for the expression of respective foreign genes. Blood was then analyzed differentially by Sysmex.

EXAMPLE 7

Induction and Tissue Specificity of PBSF Expression

A. Induction of PBSF Expression

Figure 6:
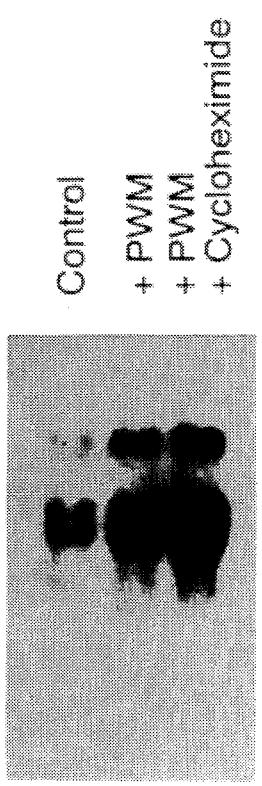
FIG. 6 shows a Northern analysis of PBSF expression in peripheral blood lymphocytes. The control lane shows expression levels in the absence of inducers for cytokine expression, the middle lane shows expression in the presence of pokeweed mitogen (PWM), the right lane shows expression in the presence of PWM and cycloheximide.

PBSF expression under various inducing conditions was studied to determine whether P64 expression could be induced under condition generally known to stimulate the synthesis of cytokines. RNA was isolated from peripheral blood lymphocytes which was untreated or treated with poke weed mitogen (PWM), or PWM and cycloheximide as described in Example 1B and 1C. RNA was electrophoresed on a 1.2% agarose gel and probed with the PBSF cDNA clone from the oligo dT primed peripheral blood lymphocyte library labelled with $^{32}p$ by random priming method. The results are shown in FIG. 6.

Figure 7:
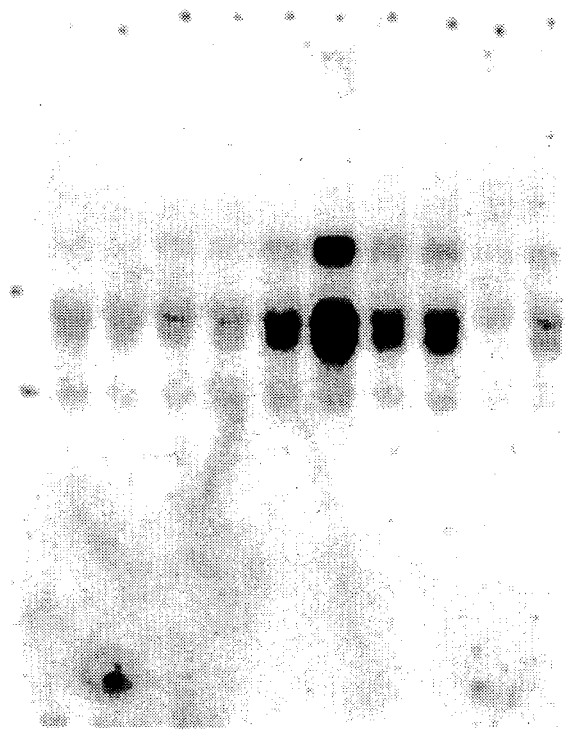
FIG. 7 shows a Northern Analysis of PBSF expression during monocytic differentiation of human leukemic cell lines. Lane 1, ML-1, untreated; Lane 2, ML-1 treated with PMA; Lane 3, ML-1 treated with tumor necrosis factor (TNF); Lane 4, ML-1 treated with TNF and IL-6; Lane 5, HL-60, untreated; Lane 6, HL-60 treated with PMA; Lane 7, HL-60 treated with TNF; Lane 8, HL-6-treated with TNF and IL-6.

The expression of PBSF during induced differentiation of human leukemic cells was also analyzed by Northern blot. Three myelomonocytic cell lines of human origin (HL-60, ATCC No. CCL-240, KG-1, ATCC No. CCL-246, and ML-1, (Samal et al. *Leuk. Res.* 14, 575–580 (1990)) were induced to differentiate towards macrophages by treatment with either PMA, tumor necrosis factor (TNF) or TNF and IL-6. RNA was isolated and subjected to a Northern analysis as described for PWM and cycloheximide induction. The results are shown in FIG. 7. The highest levels of PBSF mRNA synthesis were observed in HL-60 cells induced by PMA. Only very 10 low levels of P64 mRNA were detected under any conditions in KG-1 and ML-1 cells.

B. Tissue specificity of PBSF Expression

Tissue specific expression of P64 was determined both by Northern analysis and RT/PCR. About 10 μg of total RNA from human brain, lungs, and placenta (all purchased from Clontech Laboratories) and 10 μg of RNA from HeLa and PMA-activated Jurkat cells were analyzed by Northern blots (Lehrach H. et al, Biochem. 16, 4743 (1977)) using the $^{32}p$ labeled PBSF clone described in Section A as a probe. PBSF RNA was found to be present in lung tissue and in HeLa cells.

Similar results were obtained using RT/PCR analysis (Noonan et al. *Nucleic Acid Res.* 16, 10366 (1988)). First strand cDNA was synthesized as described in Example 1E from about 10 μg of total RNA from HeLa cells and from human brain, heart, skeletal muscle, spleen, thymus, bone marrow, kidney, liver, lungs, testis, and placenta. PBSF mRNA was amplified by an automated thermocycler (Perkin Elmer Cetus,) using two primers having the following sequences:

5' AGGGATGGAACTACATTC 3' (sense primer); and
5' TCATAGCTATCGCTGACC 3' (antisense primer).

Figure 8:
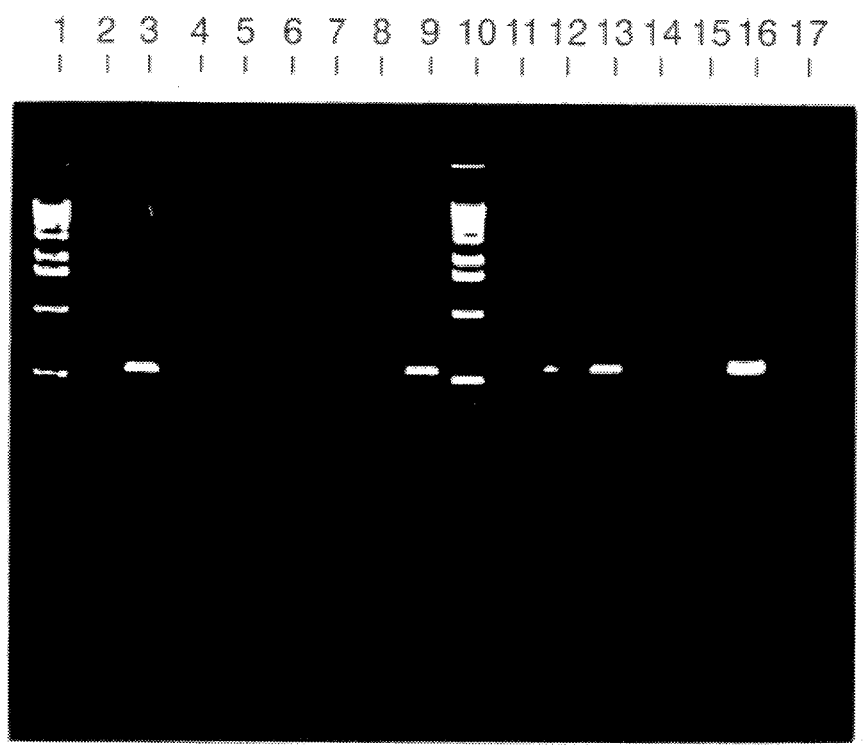
FIG. 8 shows the pattern of PBSF expression in various tissues analyzed by reverse transcriptase and PCR. Lanes 1 and 10, molecular weight markers; Lane 2, brain; Lane 3, HeLa cells; Lane 4, heart; Lane 5, skeletal muscle; Lane 6, spleen; Lane 7, pancreas; Lane 8, thymus; Lane 9, bone marrow; Lane 11, kidney; Lane 12, liver; Lane 13, lung; Lane 14, testis; Lane 15, placenta; Lane 16, peripheral blood lymphocytes; Lane 17, negative control.

The sense primer sequence corresponds to nucleotides 323–340 in SEQ. ID. NO. 1 and the antisense primer is complementary to nucleotides 855–872 in SEQ. ID. NO. 1. The primers were hybridized under stringent conditions for a total of 27 cycles such that the annealing temperature was about 2° C. below melting temperature ($T_m$) of the primer-template complex. The resulting primer extension products were analyzed on a 1.5% agarose gel. The results are shown in FIG. 8. PBSF mRNA was expressed in HeLa cells, bone marrow, liver and lungs and barely detectable in other tissues tested except at 40 or more cycles. The identity of the amplified products as PBSF was verified by a Southern blot analysis. A 1190 bp Hind III/Xba I subfragment of the PBSF clone labelled with $^{32}p$ by random priming was used as a probe.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. An isolated and purified DNA molecule encoding a polypeptide having the activity of stimulating the production of pre-B cells wherein said molecule is selected from the group consisting of:

a) the DNA molecule as set out in SEQ ID NO. 1 and its complementary strand; and b) DNA molecules which are degenerate to the molecules in (a) and encode polypeptides having the activity of simulating the production of pre-B cells.

2. The DNA molecule of claim 1 which is cDNA.

3. The DNA molecule of claim 1 which is genomic DNA.

4. The DNA molecule of claim 1 which is synthetic DNA.

5. The DNA molecule of claim 1 which is covalently associated with a detectable label.

6. The DNA molecule of claim 1 which includes one or more codons preferred for expression in *E. coli* host cells.

7. A DNA molecule consisting of a sequence as shown in SEQ. ID. NO. 1.

8. An isolated and purified DNA molecule encoding a polypeptide comprising an amine add sequence from residue 15 to 491 as set forth in SEQ ID NO: 2, said polypeptide optionally having an additional methionine residue at the amino terminus.

9. An isolated and purified DNA molecule encoding a polypeptide comprising an amine add sequence from residue 32 to 491 as set forth in SEQ ID NO: 2, said polypeptide optionally having an additional methionine residue at the amino terminus.

10. A DNA expression vector comprising a DNA molecule according to any of claims 1, 7, 8 or 9.

11. A procaryotic or eucaryotic host cell stably transformed or transfected with a DNA vector or claim 10.

12. A process for the production of a polypeptide, said process comprising:
   growing, under suitable nutrient conditions, procaryotic or eucaryotic host cells transformed or transfected with a DNA molecule of claim 1, 8 or 9 in a manner allowing expression of said polypeptide; and
   isolating said polypeptide.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2376 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 28..1498

( x i ) SEQUENCE DESCRIPTION: SEQ ID NO:1:

```
CGCGCGGCCC CTGTCCTCCG GCCCGAG ATG AAT CCT GCG GCA GAA GCC GAG           51
                                Met Asn Pro Ala Ala Glu Ala Glu
                                  1               5

TTC AAC ATC CTC CTG GCC ACC GAC TCC TAC AAG GTT ACT CAC TAT AAA         99
Phe Asn Ile Leu Leu Ala Thr Asp Ser Tyr Lys Val Thr His Tyr Lys
         10                  15                  20

CAA TAT CCA CCC AAC ACA AGC AAA GTT TAT TCC TAC TTT GAA TGC CGT        147
Gln Tyr Pro Pro Asn Thr Ser Lys Val Tyr Ser Tyr Phe Glu Cys Arg
 25                  30                  35                  40

GAA AAG AAG ACA GAA AAC TCC AAA TTA AGG AAG GTG AAA TAT GAG GAA        195
Glu Lys Lys Thr Glu Asn Ser Lys Leu Arg Lys Val Lys Tyr Glu Glu
                     45                  50                  55

ACA GTA TTT TAT GGG TTG CAG TAC ATT CTT AAT AAG TAC TTA AAA GGT        243
Thr Val Phe Tyr Gly Leu Gln Tyr Ile Leu Asn Lys Tyr Leu Lys Gly
                 60                  65                  70

AAA GTA GTA ACC AAA GAG AAA ATC CAG GAA GCC AAA GAT GTC TAC AAA        291
Lys Val Val Thr Lys Glu Lys Ile Gln Glu Ala Lys Asp Val Tyr Lys
             75                  80                  85

GAA CAT TTC CAA GAT GAT GTC TTT AAT GAA AAG GGA TGG AAC TAC ATT        339
Glu His Phe Gln Asp Asp Val Phe Asn Glu Lys Gly Trp Asn Tyr Ile
```

|   |   |   |   |   |   |   |   |   |   |   |   |   |   |   |   |   |
|---|---|---|---|---|---|---|---|---|---|---|---|---|---|---|---|---|
| | | 90 | | | | | 95 | | | | | 100 | | | | |
| CTT | GAG | AAG | TAT | GAT | GGG | CAT | CTT | CCA | ATA | GAA | ATA | AAA | GCT | GTT | CCT | 387 |
| Leu | Glu | Lys | Tyr | Asp | Gly | His | Leu | Pro | Ile | Glu | Ile | Lys | Ala | Val | Pro | |
| 105 | | | | | 110 | | | | | 115 | | | | | 120 | |
| GAG | GGC | TTT | GTC | ATT | CCC | AGA | GGA | AAT | GTT | CTC | TTC | ACG | GTG | GAA | AAC | 435 |
| Glu | Gly | Phe | Val | Ile | Pro | Arg | Gly | Asn | Val | Leu | Phe | Thr | Val | Glu | Asn | |
| | | | | 125 | | | | | 130 | | | | | 135 | | |
| ACA | GAT | CCA | GAG | TGT | TAC | TGG | CTT | ACA | AAT | TGG | ATT | GAG | ACT | ATT | CTT | 483 |
| Thr | Asp | Pro | Glu | Cys | Tyr | Trp | Leu | Thr | Asn | Trp | Ile | Glu | Thr | Ile | Leu | |
| | | | 140 | | | | | 145 | | | | | 150 | | | |
| GTT | CAG | TCC | TGG | TAT | CCA | ATC | ACA | GTG | GCC | ACA | AAT | TCT | AGA | GAG | CAG | 531 |
| Val | Gln | Ser | Trp | Tyr | Pro | Ile | Thr | Val | Ala | Thr | Asn | Ser | Arg | Glu | Gln | |
| | | 155 | | | | | 160 | | | | | 165 | | | | |
| AAG | AAA | ATA | TTG | GCC | AAA | TAT | TTG | TTA | GAA | ACT | TCT | GGT | AAC | TTA | GAT | 579 |
| Lys | Lys | Ile | Leu | Ala | Lys | Tyr | Leu | Leu | Glu | Thr | Ser | Gly | Asn | Leu | Asp | |
| | 170 | | | | | 175 | | | | | 180 | | | | | |
| GGT | CTG | GAA | TAC | AAG | TTA | CAT | GAT | TTT | GGC | TAC | AGA | GGA | GTC | TCT | TCC | 627 |
| Gly | Leu | Glu | Tyr | Lys | Leu | His | Asp | Phe | Gly | Tyr | Arg | Gly | Val | Ser | Ser | |
| 185 | | | | | 190 | | | | | 195 | | | | | 200 | |
| CAA | GAG | ACT | GCT | GGC | ATA | GGA | GCA | TCT | GCT | CAC | TTG | GTT | AAC | TTC | AAA | 675 |
| Gln | Glu | Thr | Ala | Gly | Ile | Gly | Ala | Ser | Ala | His | Leu | Val | Asn | Phe | Lys | |
| | | | | 205 | | | | | 210 | | | | | 215 | | |
| GGA | ACA | GAT | ACA | GTA | GCA | GGA | CTT | GCT | CTA | ATT | AAA | AAA | TAT | TAT | GGA | 723 |
| Gly | Thr | Asp | Thr | Val | Ala | Gly | Leu | Ala | Leu | Ile | Lys | Lys | Tyr | Tyr | Gly | |
| | | | 220 | | | | | 225 | | | | | 230 | | | |
| ACG | AAA | GAT | CCT | GTT | CCA | GGC | TAT | TCT | GTT | CCA | GCA | GCA | GAA | CAC | AGT | 771 |
| Thr | Lys | Asp | Pro | Val | Pro | Gly | Tyr | Ser | Val | Pro | Ala | Ala | Glu | His | Ser | |
| | | 235 | | | | | 240 | | | | | 245 | | | | |
| ACC | ATA | ACA | GCT | TGG | GGG | AAA | GAC | CAT | GAA | AAA | GAT | GCT | TTT | GAA | CAT | 819 |
| Thr | Ile | Thr | Ala | Trp | Gly | Lys | Asp | His | Glu | Lys | Asp | Ala | Phe | Glu | His | |
| | 250 | | | | | 255 | | | | | 260 | | | | | |
| ATT | GTA | ACA | CAG | TTT | TCA | TCA | GTG | CCT | GTA | TCT | GTG | GTC | AGC | GAT | AGC | 867 |
| Ile | Val | Thr | Gln | Phe | Ser | Ser | Val | Pro | Val | Ser | Val | Val | Ser | Asp | Ser | |
| 265 | | | | | 270 | | | | | 275 | | | | | 280 | |
| TAT | GAC | ATT | TAT | AAT | GCG | TGT | GAG | AAA | ATA | TGG | GGT | GAA | GAT | CTA | AGA | 915 |
| Tyr | Asp | Ile | Tyr | Asn | Ala | Cys | Glu | Lys | Ile | Trp | Gly | Glu | Asp | Leu | Arg | |
| | | | | 285 | | | | | 290 | | | | | 295 | | |
| CAT | TTA | ATA | GTA | TCG | AGA | AGT | ACA | CAG | GCA | CCA | CTA | ATA | ATC | AGA | CCT | 963 |
| His | Leu | Ile | Val | Ser | Arg | Ser | Thr | Gln | Ala | Pro | Leu | Ile | Ile | Arg | Pro | |
| | | | 300 | | | | | 305 | | | | | 310 | | | |
| GAT | TCT | GGA | AAC | CCT | CTT | GAC | ACT | GTG | TTA | AAG | GTT | TTG | GAG | ATT | TTA | 1011 |
| Asp | Ser | Gly | Asn | Pro | Leu | Asp | Thr | Val | Leu | Lys | Val | Leu | Glu | Ile | Leu | |
| | | 315 | | | | | 320 | | | | | 325 | | | | |
| GGT | AAG | AAG | TTT | CCT | GTT | ACT | GAG | AAC | TCA | AAG | GGT | TAC | AAG | TTG | CTG | 1059 |
| Gly | Lys | Lys | Phe | Pro | Val | Thr | Glu | Asn | Ser | Lys | Gly | Tyr | Lys | Leu | Leu | |
| | 330 | | | | | 335 | | | | | 340 | | | | | |
| CCA | CCT | TAT | CTT | AGA | GTT | ATT | CAA | GGG | GAT | GGA | GTA | GAT | ATT | AAT | ACC | 1107 |
| Pro | Pro | Tyr | Leu | Arg | Val | Ile | Gln | Gly | Asp | Gly | Val | Asp | Ile | Asn | Thr | |
| 345 | | | | | 350 | | | | | 355 | | | | | 360 | |
| TTA | CAA | GAG | ATT | GTA | GAA | GGC | ATG | AAA | CAA | AAA | ATG | TGG | AGT | ATT | GAA | 1155 |
| Leu | Gln | Glu | Ile | Val | Glu | Gly | Met | Lys | Gln | Lys | Met | Trp | Ser | Ile | Glu | |
| | | | | 365 | | | | | 370 | | | | | 375 | | |
| AAT | ATT | GCC | TTC | GGT | TCT | GGT | GGA | GGT | TTG | CTA | CAG | AAG | TTG | ACA | AGA | 1203 |
| Asn | Ile | Ala | Phe | Gly | Ser | Gly | Gly | Gly | Leu | Leu | Gln | Lys | Leu | Thr | Arg | |
| | | | 380 | | | | | 385 | | | | | 390 | | | |
| GAT | CTC | TTG | AAT | TGT | TCC | TTC | AAG | TGT | AGC | TAT | GTT | GTA | ACT | AAT | GGC | 1251 |
| Asp | Leu | Leu | Asn | Cys | Ser | Phe | Lys | Cys | Ser | Tyr | Val | Val | Thr | Asn | Gly | |
| | | 395 | | | | | 400 | | | | | 405 | | | | |
| CTT | GGG | ATT | AAC | GTC | TTC | AAG | GAC | CCA | GTT | GCT | GAT | CCC | AAC | AAA | AGG | 1299 |
| Leu | Gly | Ile | Asn | Val | Phe | Lys | Asp | Pro | Val | Ala | Asp | Pro | Asn | Lys | Arg | |

|     |     |     |     | 410 |     |     |     | 415 |     |     |     | 420 |     |     |     |      |
|-----|-----|-----|-----|-----|-----|-----|-----|-----|-----|-----|-----|-----|-----|-----|-----|------|
| TCC | AAA | AAG | GGC | CGA | TTA | TCT | TTA | CAT | AGG | ACG | CCA | GCA | GGG | AAT | TTT | 1347 |
| Ser | Lys | Lys | Gly | Arg | Leu | Ser | Leu | His | Arg | Thr | Pro | Ala | Gly | Asn | Phe |      |
| 425 |     |     |     | 430 |     |     |     |     |     | 435 |     |     |     |     | 440 |      |
| GTT | ACA | CTG | GAG | GAA | GGA | AAA | GGA | GAC | CTT | GAG | GAA | TAT | GGT | CAG | GAT | 1395 |
| Val | Thr | Leu | Glu | Glu | Gly | Lys | Gly | Asp | Leu | Glu | Glu | Tyr | Gly | Gln | Asp |      |
|     |     |     |     |     | 445 |     |     |     |     | 450 |     |     |     |     | 455 |      |
| CTT | CTC | CAT | ACT | GTC | TTC | AAG | AAT | GGC | AAG | GTG | ACA | AAA | AGC | TAT | TCA | 1443 |
| Leu | Leu | His | Thr | Val | Phe | Lys | Asn | Gly | Lys | Val | Thr | Lys | Ser | Tyr | Ser |      |
|     |     | 460 |     |     |     |     |     | 465 |     |     |     |     | 470 |     |     |      |
| TTT | GAT | GAA | ATA | AGA | AAA | AAT | GCA | CAG | CTG | AAT | ATT | GAA | CTG | GAA | GCA | 1491 |
| Phe | Asp | Glu | Ile | Arg | Lys | Asn | Ala | Gln | Leu | Asn | Ile | Glu | Leu | Glu | Ala |      |
|     |     | 475 |     |     |     | 480 |     |     |     |     | 485 |     |     |     |     |      |
| GCA | CAT | C ATTAGGCTTT | | ATGACTGGGT | | GTGTGTTGTG | | TGTATGTAAT | | ACATAATGTT | | | | | | 1548 |
| Ala | His |     |     |     |     |     |     |     |     |     |     |     |     |     |     |      |
|     | 490 |     |     |     |     |     |     |     |     |     |     |     |     |     |     |      |

| TATTGTACAG | ATGTGTGGGG | TTTGTGTTTT | ATGATACATT | ACAGCCAAAT | TATTTGTTGG | 1608 |
| TTTATGGACA | TACTGCCCTT | TCATTTTTTT | TCTTTTCCAG | TGTTTAGGTG | ATCTCAAATT | 1668 |
| AGGAAATGCA | TTTAACCATG | TAAAAGATGA | GTGCTAAAGT | AAGCTTTTA  | GGGCCCTTTG | 1728 |
| CCAATAGGTA | GTCATTCAAT | CTGGTATTGA | TCTTTTCACA | AATAACAGAA | CTGAGAAACT | 1788 |
| TTTATATATA | ACTGATGATC | ACATAAAACA | GATTTGCATA | AAATTACCAT | GATTGCTTTA | 1848 |
| TGTTTATATT | TAACTTGTAT | TTTTGTACAA | ACAAGATTGT | GTAAGATATA | TTTGAAGTTT | 1908 |
| CAGTGATTTA | ACAGTCTTTC | CAACTTTTCA | TGATTTTAT  | GAGCACAGAC | TTTCAAGAAA | 1968 |
| ATACTTGAAA | ATAAATTACA | TTGCCTTTTG | TCCATTAATC | AGCAAATAAA | ACATGGCCTT | 2028 |
| AACAAAGTTG | TTTGTGTTAT | TGTACAATTT | GAAAATTATG | TCGGGACATA | CCCTATAGAA | 2088 |
| TTACTAACCT | TACTGCCCCT | TGTAGAATAT | GTATTAATCA | TTCTACATTA | AAGAAAATAA | 2148 |
| TGGTTCTTAC | TGGAATGTCT | AGGCACTGTA | CAGTTATTAT | ATATCTTGGT | TGTTGTATTG | 2208 |
| TACCAGTGAA | ATGCCAAATT | TGAAAGGCCT | GTACTGCAAT | TTTATATGTC | AGAGATTGCC | 2268 |
| TGTGGCTCTA | ATATGCACCT | CAAGATTTTA | AGGAGATAAT | GTTTTAGAG  | AGAATTTCTG | 2328 |
| CTTCCACTAT | AGAATATATA | CATAAATGTA | AATACTTAC  | AAAAGTGG   |            | 2376 |

( 2 ) INFORMATION FOR SEQ ID NO:2:

( i ) SEQUENCE CHARACTERISTICS:
        ( A ) LENGTH: 490 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asn | Pro | Ala | Ala | Glu | Ala | Glu | Phe | Asn | Ile | Leu | Leu | Ala | Thr | Asp |
| 1   |     |     |     | 5   |     |     |     |     | 10  |     |     |     |     | 15  |     |
| Ser | Tyr | Lys | Val | Thr | His | Tyr | Lys | Gln | Tyr | Pro | Pro | Asn | Thr | Ser | Lys |
|     |     |     | 20  |     |     |     |     | 25  |     |     |     |     | 30  |     |     |
| Val | Tyr | Ser | Tyr | Phe | Glu | Cys | Arg | Glu | Lys | Lys | Thr | Glu | Asn | Ser | Lys |
|     |     | 35  |     |     |     |     | 40  |     |     |     |     | 45  |     |     |     |
| Leu | Arg | Lys | Val | Lys | Tyr | Glu | Glu | Thr | Val | Phe | Tyr | Gly | Leu | Gln | Tyr |
|     | 50  |     |     |     |     | 55  |     |     |     |     | 60  |     |     |     |     |
| Ile | Leu | Asn | Lys | Tyr | Leu | Lys | Gly | Lys | Val | Val | Thr | Lys | Glu | Lys | Ile |
| 65  |     |     |     |     | 70  |     |     |     |     | 75  |     |     |     |     | 80  |
| Gln | Glu | Ala | Lys | Asp | Val | Tyr | Lys | Glu | His | Phe | Gln | Asp | Asp | Val | Phe |
|     |     |     |     | 85  |     |     |     |     | 90  |     |     |     |     | 95  |     |

```
Asn  Glu  Lys  Gly  Trp  Asn  Tyr  Ile  Leu  Glu  Lys  Tyr  Asp  Gly  His  Leu
               100                      105                      110

Pro  Ile  Glu  Ile  Lys  Ala  Val  Pro  Glu  Gly  Phe  Val  Ile  Pro  Arg  Gly
               115                      120                      125

Asn  Val  Leu  Phe  Thr  Val  Glu  Asn  Thr  Asp  Pro  Glu  Cys  Tyr  Trp  Leu
     130                      135                      140

Thr  Asn  Trp  Ile  Glu  Thr  Ile  Leu  Val  Gln  Ser  Trp  Tyr  Pro  Ile  Thr
145                           150                      155                      160

Val  Ala  Thr  Asn  Ser  Arg  Glu  Gln  Lys  Lys  Ile  Leu  Ala  Lys  Tyr  Leu
               165                      170                      175

Leu  Glu  Thr  Ser  Gly  Asn  Leu  Asp  Gly  Leu  Glu  Tyr  Lys  Leu  His  Asp
               180                      185                      190

Phe  Gly  Tyr  Arg  Gly  Val  Ser  Ser  Gln  Glu  Thr  Ala  Gly  Ile  Gly  Ala
          195                      200                      205

Ser  Ala  His  Leu  Val  Asn  Phe  Lys  Gly  Thr  Asp  Thr  Val  Ala  Gly  Leu
          210                      215                      220

Ala  Leu  Ile  Lys  Lys  Tyr  Gly  Thr  Lys  Asp  Pro  Val  Pro  Gly  Tyr
225                           230                      235                      240

Ser  Val  Pro  Ala  Ala  Glu  His  Ser  Thr  Ile  Thr  Ala  Trp  Gly  Lys  Asp
                    245                      250                      255

His  Glu  Lys  Asp  Ala  Phe  Glu  His  Ile  Val  Thr  Gln  Phe  Ser  Ser  Val
               260                      265                      270

Pro  Val  Ser  Val  Val  Ser  Asp  Ser  Tyr  Asp  Ile  Tyr  Asn  Ala  Cys  Glu
          275                      280                      285

Lys  Ile  Trp  Gly  Glu  Asp  Leu  Arg  His  Leu  Ile  Val  Ser  Arg  Ser  Thr
     290                      295                      300

Gln  Ala  Pro  Leu  Ile  Ile  Arg  Pro  Asp  Ser  Gly  Asn  Pro  Leu  Asp  Thr
305                           310                      315                      320

Val  Leu  Lys  Val  Leu  Glu  Ile  Leu  Gly  Lys  Lys  Phe  Pro  Val  Thr  Glu
                    325                      330                      335

Asn  Ser  Lys  Gly  Tyr  Lys  Leu  Leu  Pro  Pro  Tyr  Leu  Arg  Val  Ile  Gln
               340                      345                      350

Gly  Asp  Gly  Val  Asp  Ile  Asn  Thr  Leu  Gln  Glu  Ile  Val  Glu  Gly  Met
          355                      360                      365

Lys  Gln  Lys  Met  Trp  Ser  Ile  Glu  Asn  Ile  Ala  Phe  Gly  Ser  Gly  Gly
     370                      375                      380

Gly  Leu  Leu  Gln  Lys  Leu  Thr  Arg  Asp  Leu  Leu  Asn  Cys  Ser  Phe  Lys
385                      390                      395                      400

Cys  Ser  Tyr  Val  Val  Thr  Asn  Gly  Leu  Gly  Ile  Asn  Val  Phe  Lys  Asp
                    405                      410                      415

Pro  Val  Ala  Asp  Pro  Asn  Lys  Arg  Ser  Lys  Lys  Gly  Arg  Leu  Ser  Leu
               420                      425                      430

His  Arg  Thr  Pro  Ala  Gly  Asn  Phe  Val  Thr  Leu  Glu  Glu  Gly  Lys  Gly
          435                      440                      445

Asp  Leu  Glu  Glu  Tyr  Gly  Gln  Asp  Leu  Leu  His  Thr  Val  Phe  Lys  Asn
     450                      455                      460

Gly  Lys  Val  Thr  Lys  Ser  Tyr  Ser  Phe  Asp  Glu  Ile  Arg  Lys  Asn  Ala
465                      470                      475                      480

Gln  Leu  Asn  Ile  Glu  Leu  Glu  Ala  Ala  His
               485                      490
```

( 2 ) INFORMATION FOR SEQ ID NO:3:

( i ) SEQUENCE CHARACTERISTICS:
    ( A ) LENGTH: 45 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

ACTGTGGCCT GCAGCATCTC TGCACCCGCC CGCTGCCCCA GCCCC    45

( 2 ) INFORMATION FOR SEQ ID NO:4:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

CTTGCACTTG TCACAAACAG TGCACCTACT TCAAGTTCTA CAAAG    45

( 2 ) INFORMATION FOR SEQ ID NO:5:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

AACGAGGCTT ATGTGCACGA TGCACCTGTA CGATCACTGA ACTGC    45

( 2 ) INFORMATION FOR SEQ ID NO:6:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

GTGTTGCCTG CTGCCTCCCC TGCCCCAGTA CCCCCAGGAG AAGAT    45

( 2 ) INFORMATION FOR SEQ ID NO:7:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

CTGGTCCGCC CCGGACTCCA AGCTCCCATG ACCCAGACAA CGCCC    45

( 2 ) INFORMATION FOR SEQ ID NO:8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

ATGTCGACMW CSVTGCMCCH RYMYSMYCMA 30

( 2 ) INFORMATION FOR SEQ ID NO:9:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:9:

GCTTGAATTC AAGC 14

( 2 ) INFORMATION FOR SEQ ID NO:10:

( i ) SEQUENCE CHARACTERISTICS:
    ( A ) LENGTH: 8 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_binding
    ( B ) LOCATION: complement (1..8)

( x i ) SEQUENCE DESCRIPTION: SEQ ID NO:10:

CTGGAAAG 8

( 2 ) INFORMATION FOR SEQ ID NO:11:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

CTTTCCAGAC ACA 13

( 2 ) INFORMATION FOR SEQ ID NO:12:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:12:

Cys Arg Glu Lys Lys Thr Glu Asn Ser Lys Leu Arg Lys Val Lys Tyr
1     5       10      15